(12) United States Patent
Gudkov et al.

(10) Patent No.: US 9,169,207 B2
(45) Date of Patent: Oct. 27, 2015

(54) CURAXINS FOR USE IN TREATING CARCINOGEN-INDUCED CANCER

(71) Applicant: Incuron, LLC, Buffalo, NY (US)

(72) Inventors: Andrei Gudkov, East Aurura, NY (US); Katerina Gurova, Orchard Park, NY (US)

(73) Assignee: Incuron, LLC, Buffalo, NY (US)

( * ) Notice: Subject to any disclaimer, the term of this patent is extended or adjusted under 35 U.S.C. 154(b) by 0 days.

(21) Appl. No.: 14/388,126

(22) PCT Filed: Mar. 27, 2013

(86) PCT No.: PCT/US2013/034144
§ 371 (c)(1),
(2) Date: Sep. 25, 2014

(87) PCT Pub. No.: WO2013/148864
PCT Pub. Date: Oct. 3, 2013

(65) Prior Publication Data
US 2015/0045406 A1    Feb. 12, 2015

Related U.S. Application Data

(60) Provisional application No. 61/616,216, filed on Mar. 27, 2012.

(51) Int. Cl.
| | |
|---|---|
| C07D 209/88 | (2006.01) |
| A61K 31/403 | (2006.01) |
| A61K 45/06 | (2006.01) |
| G01N 33/574 | (2006.01) |

(52) U.S. Cl.
CPC ............ *C07D 209/88* (2013.01); *A61K 31/403* (2013.01); *A61K 45/06* (2013.01); *G01N 33/57415* (2013.01); *G01N 2333/4706* (2013.01); *G01N 2333/70567* (2013.01); *G01N 2333/71* (2013.01); *G01N 2333/726* (2013.01)

(58) Field of Classification Search
USPC .......................................... 514/411; 548/441
See application file for complete search history.

(56) References Cited

FOREIGN PATENT DOCUMENTS

| WO | WO-2009143290 A2 | 11/2009 |
| WO | WO-2010009171 A2 | 1/2010 |
| WO | WO-2010042445 A1 | 4/2010 |

OTHER PUBLICATIONS

Di Bussolo, V. et al., "Curaxins: A New Family of Non-Genotoxic Multitargeted Anticancer Agents," ChemMedChem, vol. 6, No. 12, pp. 2133-2136 (Oct. 28, 2011).
Garcia, H. et al., "Expression of FACT in mammalian tissues suggests its role in maintaining of undifferentiated state of cells," Oncotarget, Impact Journals LLC, United States, vol. 2, No. 10, pp. 783-796 (Oct. 1, 2011).
Gasparian, A. V. et al., "Curaxins: Anticancer Compounds that Simultaneously Suppress NF-kappa B and Activate p53 by Targeting FACT," Science Translational Medicine, vol. 3, No. 95, pp. 95106 (Aug. 2011).
Koman, I. E. et al., "Targeting FACT Complex Suppresses Mammary Tumorigenesis in Her2/neu Transgenic Mice," Cancer Prevention Research, American Association for Cancer Research, United States, vol. 5, No. 8, pp. 1025-1035 (Aug. 1, 2012).
International Search Report and Written Opinion issued for International Application No. PCT/US2013/034144 issued on Jul. 19, 2013 and mailed Jul. 31, 2013 (16 pages).

*Primary Examiner* — Kristin Vajda
(74) *Attorney, Agent, or Firm* — Morgan, Lewis & Bockius LLP

(57) ABSTRACT

The present invention relates to the treatment of breast cancer which is estrogen receptor positive (ER+) and/or human epidermal growth factor receptor 2 positive (HER2) and/or progesterone receptor positive (PR) and/or facilitates chromatin transcription positive (FACT+) with a curaxin, including curaxin 137. The present invention also pertains to a method of identifying a subject who has a breast cancer tumor and is likely to respond to treatment with a curaxin.

7 Claims, 14 Drawing Sheets

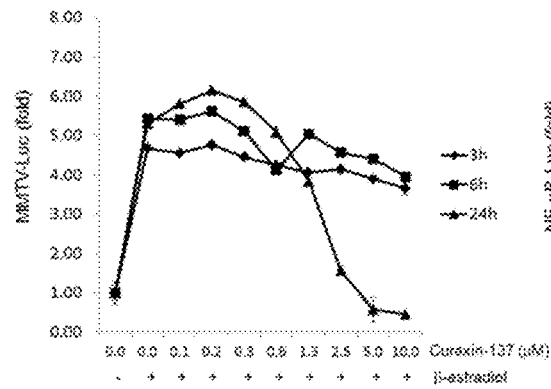
FIG. 1A
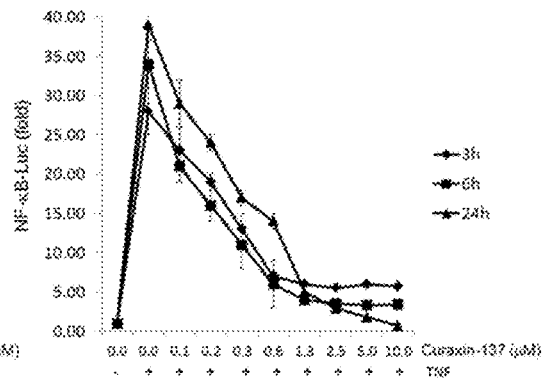
FIG. 1B
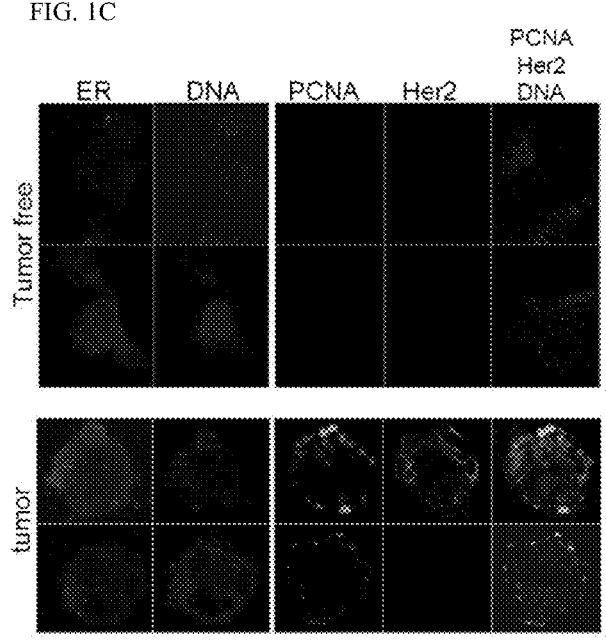
FIG. 1C
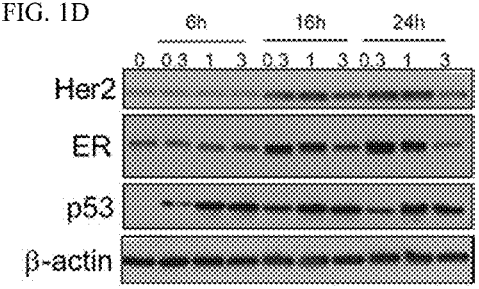
FIG. 1D
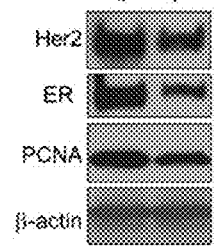
FIG. 1E
FIGs. 1A-1E FIG. 2A
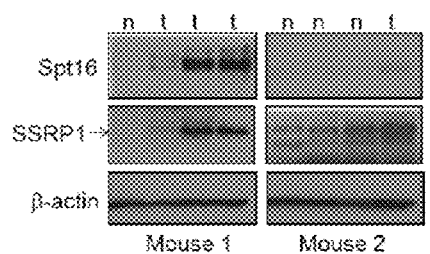
FIG. 2E
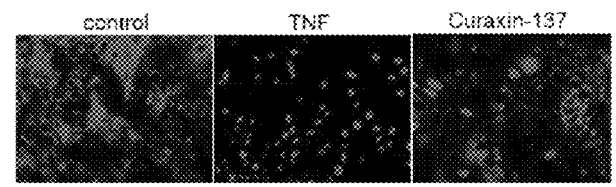
FIG. 2B
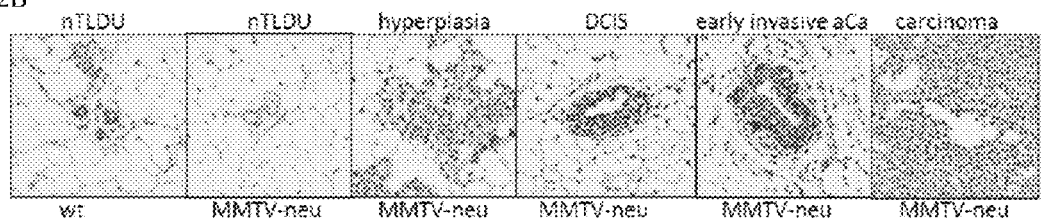
FIG. 2C
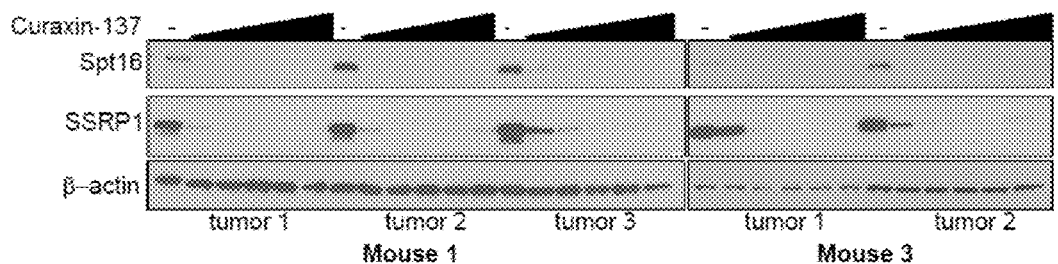
FIG. 2D
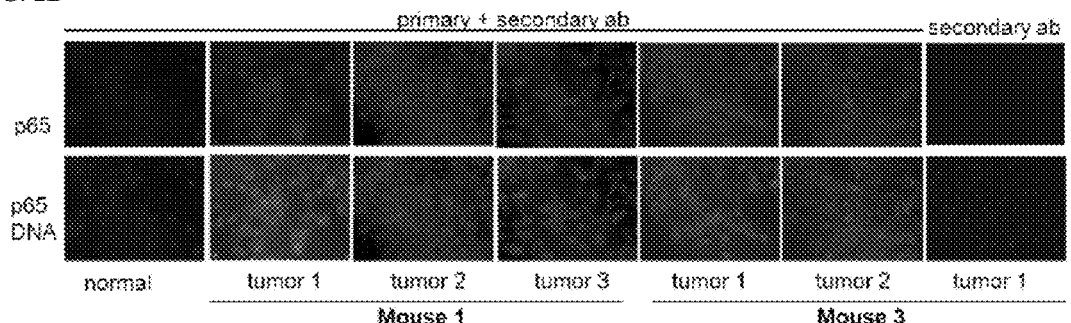
FIG. 2F
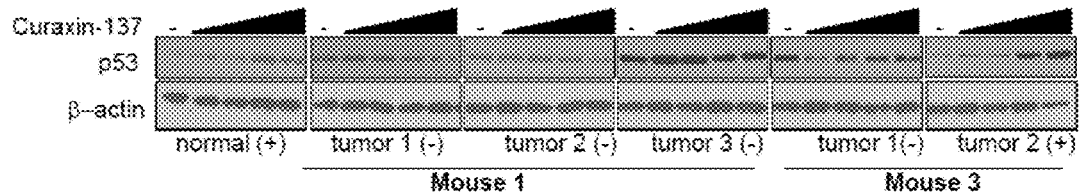
FIGs. 2A-2F FIG. 3A
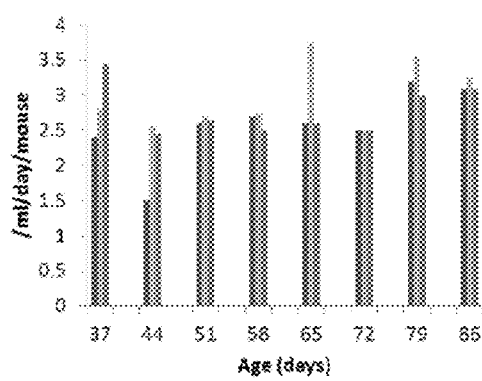
FIG. 3B
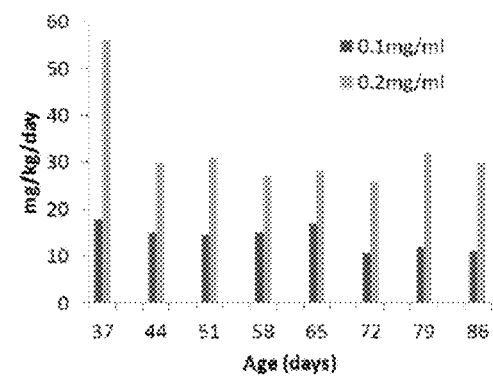
FIG. 3C
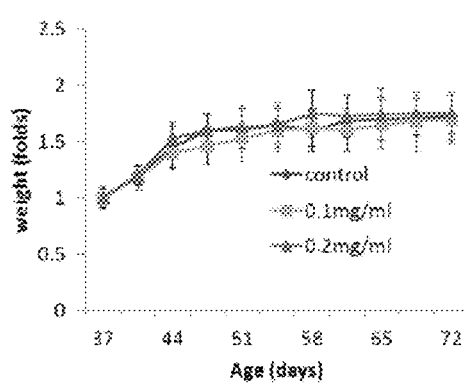
FIG. 3D
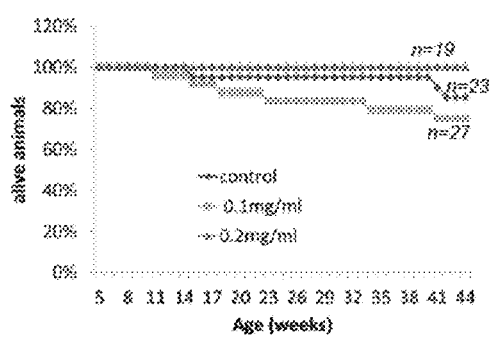
FIG. 3E
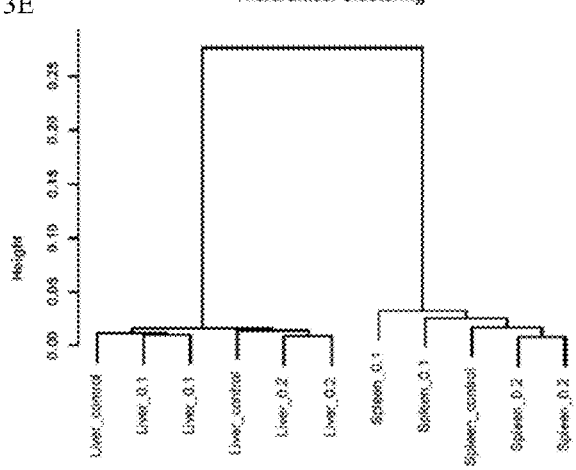
FIGs. 3A-3E FIG. 4A
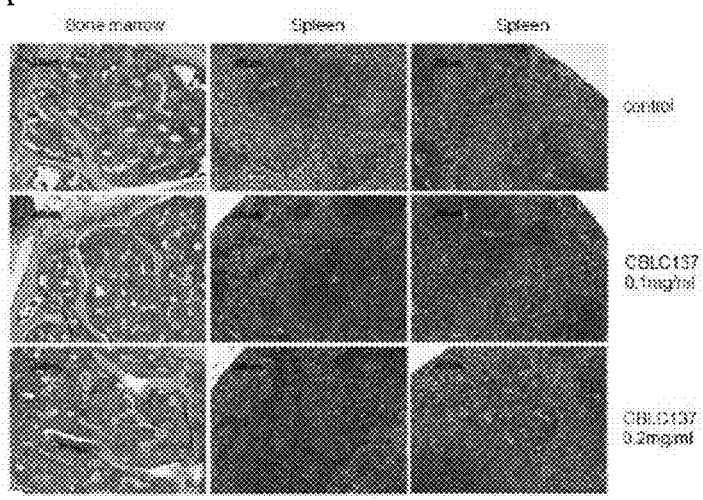
FIG. 4B
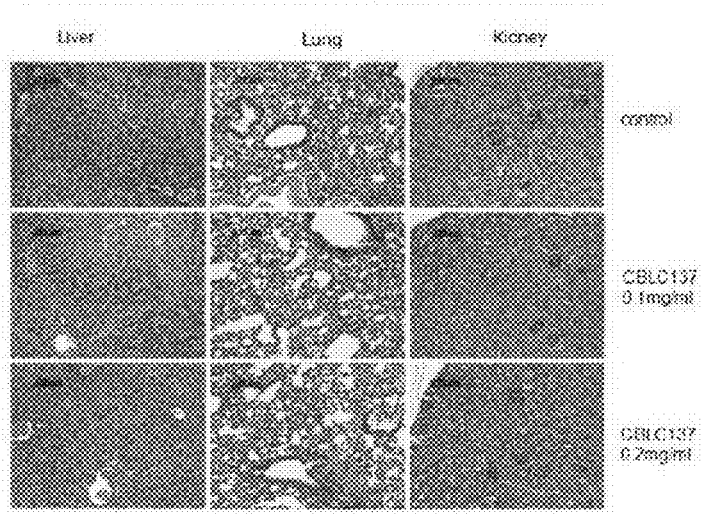
FIG. 4C
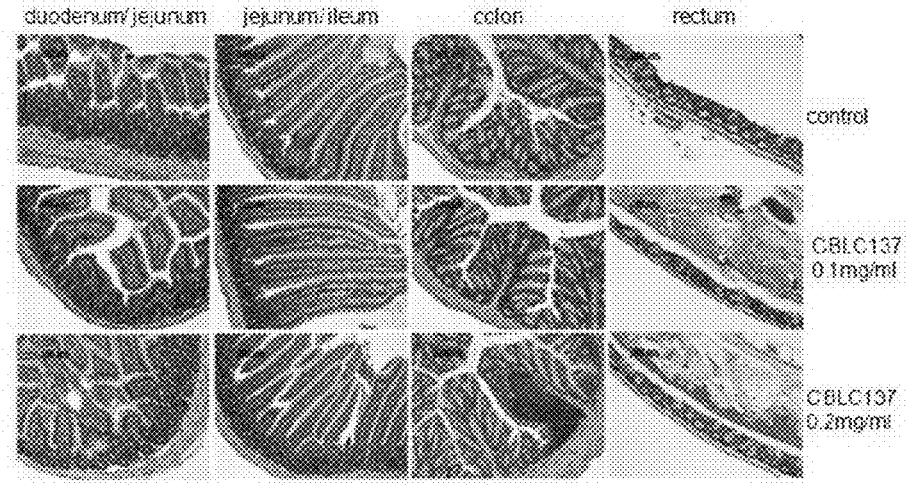
FIGs. 4A-4C FIG. 5A
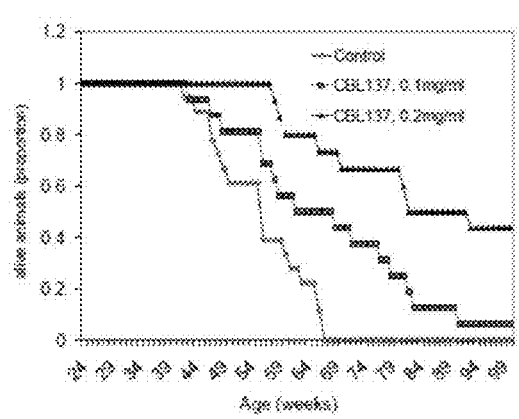
FIG. 5B
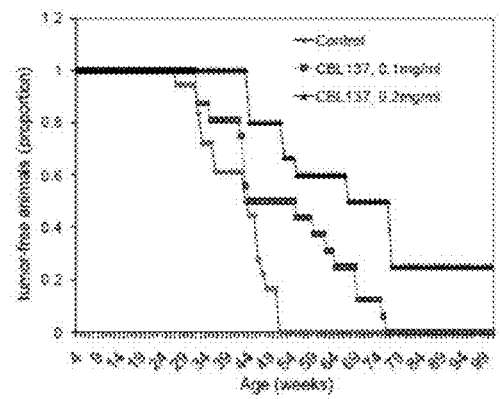
FIG. 5C
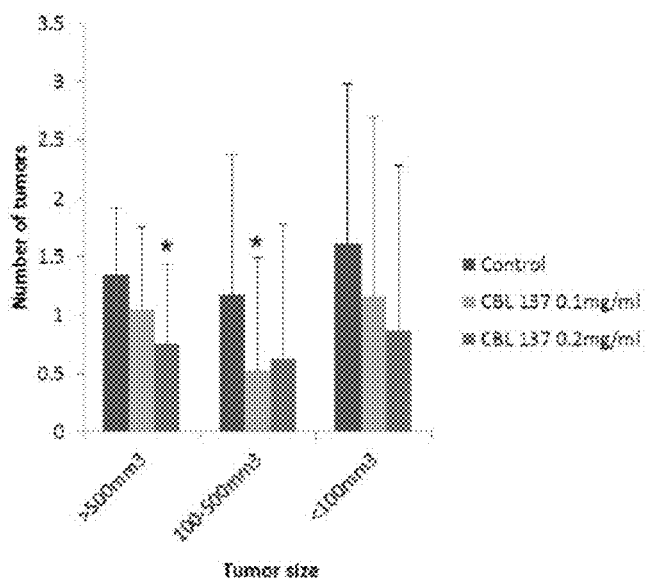
FIGs. 5A-5C

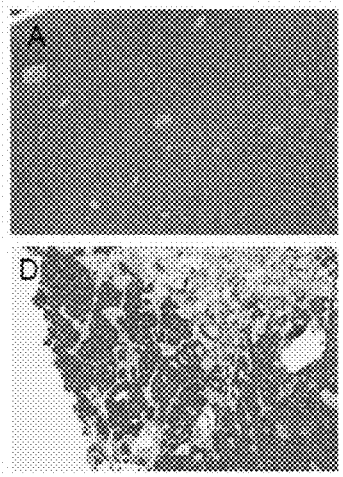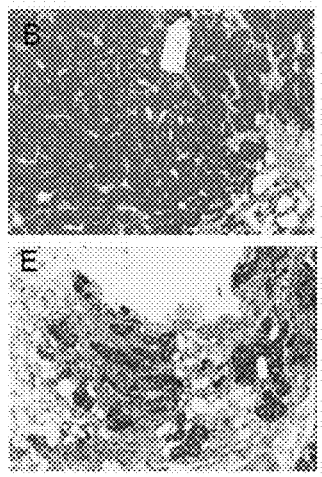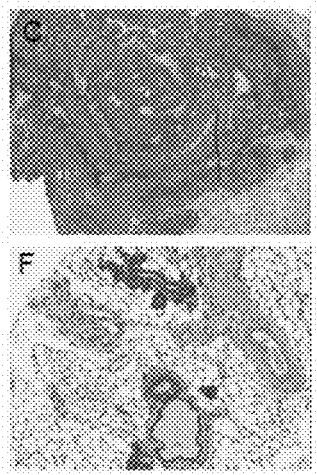
FIG. 6A  FIG. 6B  FIG. 6C
FIG. 6D  FIG. 6E  FIG. 6F
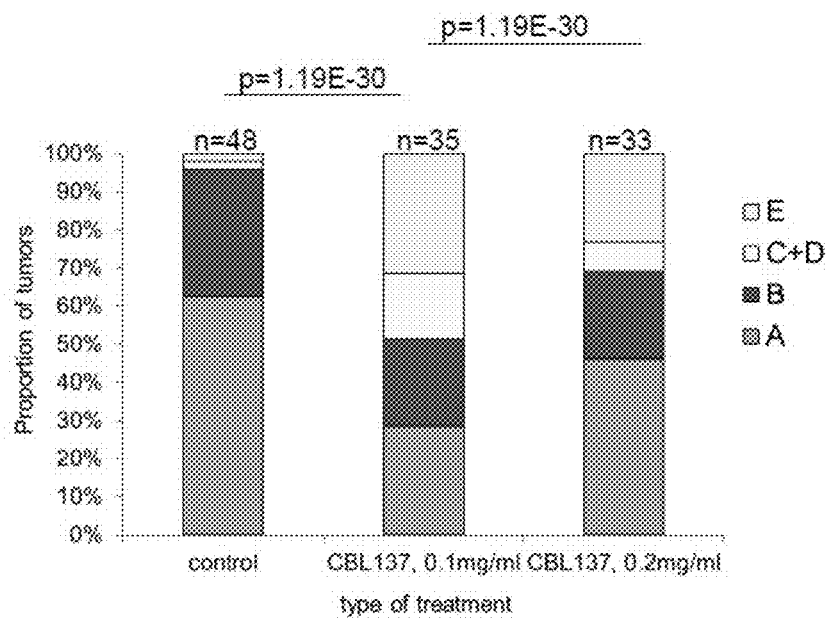
FIGs. 6A-6G

FIG. 9

| Concentration of curaxin -137 in drinking water | 0.1 mg/ml | 0.2 mg/ml |
|---|---|---|
| Plasma | 0.17+/- 0.09 | 0.33+/-0.09 |
| Liver | 0.96+/-0.55 | 1.65+/-0.5 |
| Kidney | 0.67+/-0.28 | 1. 74+/-0.33 |
| Spleen | 3.8+/-0.86 | 7.2+/-0.97 |

FIG. 10

Histopathological findings in old animals in each of treatment group (two mice per group)

| | Control | Control | Treated | Treated | Treated | Treated |
|---|---|---|---|---|---|---|
| Age | 8.5mo | 8.5mo | 16.5mo | 19mo | 17mo | 18mo |
| Mammary | adenocarcinoma | multiple adenocarcinomas | adenocarcinoma | dilated mammary acini | adenocarcinoma | adenocarcinoma |
| | no difference between control and treated mice | | | | | |
| Spleen | mild lymphoid hyperplasia | moderate lymphoid hyperplasia | mild lymphoid hyperplasia | moderate lymphoid hyperplasia | mild lymphoid hyperplasia | mild lymphoid hyperplasia |
| Lung | mild multifocal peribronchiolar lymphoid infiltrates | mild multifocal peribronchiolar lymphoid infiltrates, moderate perivascular lymphoid infiltrates | pulmonary metastases of mammary gland adenocarcinoma | mild multifocal peribronchiolar lymphoid infiltrates | metastatic adenocarcinoma | metastatic adenocarcinoma |
| Kidney | no significant changes | no significant changes | focal perivascular lymphocytic and macrophage infiltrates | focal perivascular lymphocytic and macrophage infiltrates | no significant changes | no significant changes |

FIG. 11

| Tumors / Strain | Percentage of mouse with tumors | Large intestine tumors (%) | Adenoma of perianal subcutaneous glands (%) | Uterina sarcoma (%) | Ovarian tumors (%) | Liver tumors (%) |
|---|---|---|---|---|---|---|
| C3H | 94 | 75 | 50 | 37,5 | 6 | 6 |
| CBA | 96,3 | 70,4 | 59,2 | 40,7 | 3,7 | 18,4 |
| F1 (CBAxC57Bl/6) | 83,1 | 79,3 | 24,1 | 20,7 | 17,2 | 37,9 |
| C57Bl/6 | 75,7 | 59,4 | 24,3 | 2,7 | 35,1 | 5,4 |
| BALB/c | 96,6 | 93,3 | 63,3 | - | 46,7 | 23,3 |
| DBA/2 | 70,4 | 55,5 | 25,9 | - | 82,9 | 22,2 |
| C3HA | 78,2 | 30,8 | 59,5 | - | 85,7 | 14,3 |
| AKR | 79,5 | 53,8 | 38,5 | 7,7 | 10,2 | 20,5 |

FIG. 12

| Tumors / Strain | Percentage of mouse with tumors | Liver angiosarcomas (%) | Renal adenomas (%) | Large intestine tumors (%) | Liver hemangiomas (%) | Hepatomas | Adenomas of perianal subcutaneous glands (%) | Lung tumors |
|---|---|---|---|---|---|---|---|---|
| C3H | 31 | 36 | 13 | 3 | 13 | 16 | 13 | 0 |
| CBA | 33 | 97 | 79 | 33 | 15 | 54 | 18 | 0 |
| F1 (CBAxC57Bl) | 47 | 36 | 30 | 54 | 9 | 47 | 21 | 0 |
| C57Bl/6 | 47 | 4 | 23 | 74 | 0 | 0 | 32 | 0 |
| BALB/c | 23 | 13 | 43 | 26 | 9 | 4 | 48 | 26 |
| C3HA | 28 | 7 | 14 | 4 | 0 | 11 | 14 | 0 |

FIG. 13

Consolidated table of weight of the organs extracted during necropsy from female mice

| Group | | Average weight of the mouse, g | Average weight of organ | | | | | | | | | | | | | | |
|---|---|---|---|---|---|---|---|---|---|---|---|---|---|---|---|---|---|
| | | | Lungs | | Heart | | Spleen | | Pancreas | | Kidney+adrenal glands | | Liver | | Thymus | | Uterus-ova ries |
| | | | abs, g | rel, % | abs, g | rel, % | abs, g | rel, % | abs, g | rel, % | abs, g | rel, % | abs, g | rel, % | abs, g | rel, % | abs, g | rel, % |
| Control | Mean | 31.73 | 0.25 | 0.79 | 0.11 | 0.35 | 0.09 | 0.29 | 0.08 | 0.24 | 0.38 | 1.19 | 1.35 | 4.28 | 0.04 | 0.13 | 0.39 | 1.24 |
| | SEM | | | | | | | | | | | | | | | | | |
| CBL0137 | Mean | 31.19 | 0.26 | 0.86 | 0.11 | 0.37 | 0.10 | 0.32 | 0.07 | 0.24 | 0.35 | 1.15 | 1.39 | 4.51 | 0.04 | 0.12 | 0.40 | 1.32 |
| | SEM | | | | | | | | | | | | | | | | | |
| 1,2-DMH | Mean | 27.04 | 0.22 | 0.81 | 0.12 | 0.44 | 0.14 | 0.57 | 0.08 | 0.36 | 0.36 | 1.33 | 1.24 | 4.61 | 0.03 | 0.12 | 0.77 | 2.95 |
| | SEM | | | | | | | | | | | | | | | | | |
| 1,2-DMH+ CBL0137 | Mean | 28.50 | 0.19 | 0.75 | 0.10 | 0.41 | 0.13 | 0.54 | 0.09 | 0.34 | 0.34 | 1.34 | 1.07 | 4.79 | 0.03 | 0.13 | 0.64 | 2.51 |
| | SEM | | | | | | | | | | | | | | | | | |

FIG. 14

*Consolidated table of the weight of organs extracted during necropsy from male mice.*

| Group | | Average weight of the mouse | Organ | | | | | | | | | | | | |
|---|---|---|---|---|---|---|---|---|---|---|---|---|---|---|---|
| | | | Lungs | | Heart | | Spleen | | Pancreas | | Kidney+adrenals | | Liver | | Thymus | |
| | | | abs, g | rel,% | abs, g | rel,% | abs, g | rel,% | abs, g | rel,% | abs, g | rel,% | abs, g | rel,% | abs, g | rel,% |
| Control | Mean | 38.38 | 0.33 | 0.85 | 0.15 | 0.40 | 0.10 | 0.25 | 0.08 | 0.20 | 0.68 | 1.77 | 2.05 | 5.37 | 0.04 | 0.11 |
| | SEM | 0.4863 | 0.0136 | 0.0401 | 0.0023 | 0.0063 | 0.0087 | 0.0103 | 0.0089 | 0.0100 | 0.0086 | 0.0233 | 0.0737 | 0.1893 | 0.0021 | 0.0054 |
| CBLO37 | Mean | 36.00 | 0.37 | 1.04 | 0.15 | 0.41 | 0.09 | 0.26 | 0.07 | 0.21 | 0.64 | 1.79 | 1.95 | 5.43 | 0.05 | 0.13 |
| | SEM | 0.5858 | 0.0182 | 0.0409 | 0.0023 | 0.0073 | 0.0024 | 0.0063 | 0.0041 | 0.0108 | 0.0127 | 0.0236 | 0.0872 | 0.1138 | 0.0028 | 0.0060 |
| 1,2-DMBB | Mean | 38.87 | 0.28 | 0.94 | 0.14 | 0.44 | 0.11 | 0.36 | 0.09 | 0.29 | 0.81 | 1.94 | 1.48 | 4.81 | 0.03 | 0.11 |
| | SEM | 0.4829 | 0.0136 | 0.0432 | 0.0028 | 0.0091 | 0.0059 | 0.0021 | 0.0034 | 0.0098 | 0.0324 | 0.0208 | 0.0412 | 0.1244 | 0.0028 | 0.0074 |
| 1,2-DMBB+CBLO37 | Mean | 29.64 | 0.31 | 1.07 | 0.14 | 0.48 | 0.14 | 0.49 | 0.12 | 0.34 | 0.58 | 1.84 | 1.37 | 4.69 | 0.03 | 0.12 |
| | SEM | 0.9836 | 0.0148 | 0.0673 | 0.0028 | 0.0031 | 0.0064 | 0.0413 | 0.0213 | 0.0146 | 0.0236 | 0.0559 | 0.0952 | 0.1275 | 0.0029 | 0.0064 |

FIG. 15

Macroscopic changes in organs of female mice

| Group | Number of animals | Tumors of large intestine | Tumor of perianal skin | Uterine tumors | Ovaries** | | Liver*** | | Renal tumors | Other organs |
|---|---|---|---|---|---|---|---|---|---|---|
| | | | | | Hemorrhagic neoplasms | Transparent cysts | Hemorrhagic neoplasms | From liver tissue | | |
| DMH | 39 | 20 (51.3%) | 10 (25.6%) | 19 (48.7%) | 6 (15.4%) | 6 (15.4%) | 6 (15.4%) | 1 (2.6%) | 1 (2.6%) | 1ˢ (2.6%) |
| DMH+ CBLO 137 | 44 | 12 (27.3%) | 15 (34.1%) | 18 (40.9%) | 3 (6.8%) | 5 (11.4%) | ⁻⁹ 9 (20.5%) | 1 (2.3%) | - | - |
| CBLO137 | 40 | - | - | - | - | 3 (7.7%) | - | - | - | - |
| Control | 30 | - | - | - | 1 (3.3%) | 9 (30%) | - | - | - | - |

*- neoplasms of large intestine;
** - hemorrhagic and transparent ovarian cysts;
*** - focal hemorrhagic transformations in liver and nodules from liver tissue.
ˢ - abdominal wall metastases is possible.

FIG. 16

Macroscopic changes in the organs of male mice

| Group | Number of animals | Large intestine* | Tumor of perianal skin | Renal tumors | Liver** Hemorrhagic | Liver** From liver tissue | Other organs |
|---|---|---|---|---|---|---|---|
| DMH | 37 | 22* (59.3%) | 16 (43%) | 22 (59.5%) | 1 (2.7%) | 12 (32.4%) | 1ª (2.7%) |
| DMH+ CBLO137 | 44 | 12 (27.3%) | 18 (41%) | 17 (38.6%) | 1 (2.3%) | 13 (29.5%) | - |
| CBL0137 | 39 | - | - | - | - | 22 (56.4%) | - |
| Control | 30 | - | - | - | - | 17 (56.7%) | - |

\* - polyps of large intestine;
\*\* - focal hemorrhagic transformations in liver and nodules from liver tissue
a - hemorrhagic neoplasm in mesenterium
δ - in DMH group 50% of animals were observed to have multiple polyps (from 3 to 8 per animal) in comparison with DMH+CBL0137 group

CURAXINS FOR USE IN TREATING CARCINOGEN-INDUCED CANCER

PRIORITY

This application is a U.S. National Phase Application of PCT/US2013/034144, filed Mar. 27, 2013, which claims priority to and the benefit of U.S. Provisional Application No. 61/616,216, filed Mar. 27, 2012, the contents of which are hereby incorporated by reference herein in their entireties.

FIELD OF THE INVENTION

The present invention relates to methods that are useful in treating cancer, including for example, breast cancer.

BACKGROUND

Breast cancer is a major medical concern and one of the most prevalent forms of cancer, particularly in woman. Breast cancer has the second highest mortality rate of cancers and about 15% of cancer-related deaths in women are due to breast cancer (SEER Cancer Statistics Review 1975-2005, NCI, Ries, L. A. G., et al., (eds) (2008)). It has been estimated that about 13% of women born in the United States will be diagnosed with breast cancer in their lifetime (SEER Cancer Statistics Review 1975-2005, NCI, Ries, L. A. G., et al., (eds) (2008)).

Treatment of breast cancer, as well as other cancers, can be based on the characteristics of the cancer, which in some instances involves molecular analysis of the tumor. Treatment options for breast cancer patients include surgery (e.g. lumpectomy, partial mastectomy, full mastectomy), radiation therapy and chemotherapy are also used as an alternative or additional therapy. Further, hormone therapy or endocrine therapy is used in certain cases. All of these treatment options are marred by unwelcome side effects and/or reduced efficacy, if not carefully selected for the particular tumor.

Therefore, there remains a need for methods that are useful for treating cancer and related diseases, including on a personalized basis.

BRIEF DESCRIPTION OF THE INVENTION

Accordingly, the present invention relates to improved methods for treating cancer, including, for example, breast cancer characterized by the presence of one or more of estrogen receptor (ER+), human epidermal growth factor receptor 2 (HER2+), progesterone receptor (PR+), and facilitates chromatin transcription (FACT+).

In one aspect, the present invention provides a method for treating breast cancer in a subject in need thereof comprising administering an effective amount of a compound of Formula I:

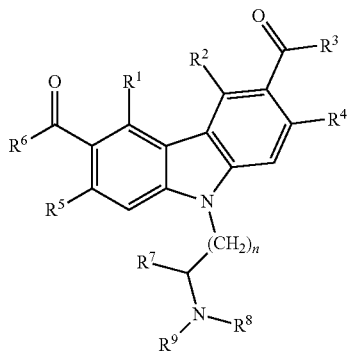

(I)

wherein each of $R^1$—$R^9$ are independently H, hydroxyl or alkyl; n is 0, 1, 2, 3, 4, or 5; or a pharmaceutically acceptable salt or hydrate thereof; and the breast cancer is one or more of estrogen receptor positive (ER+), human epidermal growth factor receptor 2 positive (HER2+), progesterone receptor positive (PR+), and facilitates chromatin transcription positive (FACT+).

In another aspect, the present invention provides a method for identifying a subject who has a breast cancer tumor and is likely to respond to treatment with a compound of Formula I, comprising evaluating the tumor comprising measuring a presence, absence, or level of at least one of ER, PR, HER2, and FACT; wherein the presence of at least one of ER, PR, HER2, and FACT indicates that the subject is likely to respond to treatment with a compound of Formula I and wherein the compound of Formula I is:

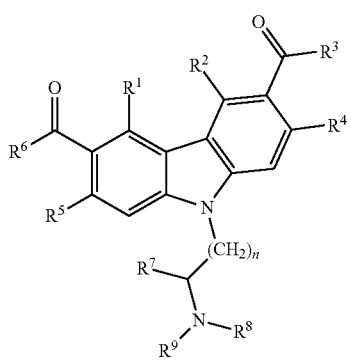

(I)

wherein each of $R^1$—$R^9$ are independently H, hydroxyl or alkyl and n is 0, 1, 2, 3, 4, or 5; or a pharmaceutically acceptable salt or hydrate thereof.

The details of the invention are set forth in the accompanying description below. Although methods and materials similar or equivalent to those described herein can be used in the practice or testing of the present invention, illustrative methods and materials are now described. Other features, objects, and advantages of the invention will be apparent from the description and from the claims. In the specification and the appended claims, the singular forms also include the plural unless the context clearly dictates otherwise. Unless defined otherwise, all technical and scientific terms used herein have the same meaning as commonly understood by one of ordinary skill in the art to which this invention belongs.

BRIEF DESCRIPTION OF THE DRAWINGS

FIGS. 1A-1E show that curaxin-137 does not affect MMTV promoter activity.

FIG. 1A-1B shows that curaxin-137 inhibits activity of the NF-κB promoter, but not the MMTV promoter. Luciferase activity was measured in lysates of MDA-MB-453-MMTV-Luc (A) and H1299-κB-Luc (B) cells treated for 3, 6 or 24 hours with different concentrations of curaxin-137 in the presence of 10 nM of R1881 (A) or 10 ng/ml TNF (B). Luciferase activity is shown as the fold-change relative to that in untreated, uninduced cells (set at 1.0). Error bars indicate standard error of three replicates.

FIG. 1C shows the effect of ex vivo curaxin-137 treatment on ER, Her2 and PCNA expression in tumor free mammary gland or tumor epithelial cells from MMTV-neu mice. Immunofluorescent staining of tumor free mammary epithelial cells (upper panel) or mammary tumor cells (lower panel) that were left untreated (−) or treated with 2 μM curaxin-137 for 24 hours (+) using antibodies against ER (red), PCNA (green) or Her2 (red). All slides were counterstained with Hoechst 33358 (blue) to visualize DNA.

FIG. 1D-1E shows western blot analysis of protein levels in cells from another MMTV-neu mouse treated with curaxin-137 ex vivo. Tumor free mammary epithelial cells were treated with the indicated concentrations of curaxin-137 for 6, 16 or 24 hours (D) and mammary tumor cells were left untreated (−) or treated with 3 μM curaxin-137 (+) for 24 h. Blots were probed with antibodies against the indicated proteins. β-actin was used as a loading control.

FIGS. 2A-2F show that FACT, p53 and NF-κB are involved in mammary carcinogenesis in MMTV-neu mice and are responsive to curaxin-137 treatment.

FIG. 2A shows increased FACT subunit expression in mammary tumors. Western blotting of total protein extracts from tumor free mammary glands (n) or mammary tumors (t) of two untreated female MMTV-neu mice with visible tumors is shown.

FIG. 2B shows FACT expression is elevated in mammary glands of MMTV-neu animals at different stages of tumor formation. Immunohistochemical staining with anti-SSRP1 antibody of sections of mammary gland tissue from wild type (wt) and MMTV-neu animals and lesions of different stages from MMTV-new animals. TLDU—terminal lobular-ductal unit. DCIS—ductal carcinoma in situ.

FIG. 2C shows that curaxin-137 treatment depletes the soluble pool of FACT in mammary tumor cells of MMTV-neu mice. Western blotting of soluble extracts of cells isolated from several different tumors of two mice is shown. Disaggregated tumor cells were left untreated (−) or treated ex vivo with increasing concentrations of curaxin-137 (1-10 μM) for 1 h.

FIG. 2D shows increased level of NF-κB in mammary tumors of MMTV-neu mice as compared to normal mammary cells Immunofluorescent staining of cells with antibodies to p65 (green) and of DNA with Hoechst 33358 (blue) is shown.

FIG. 2E shows that curaxin-137 induces nuclear accumulation of NF-κB in mammary tumor cells from MMTV-neu mice Immunofluorescent staining with anti-p65 antibody of disaggregated tumor cells treated ex vivo with 2 μM curaxin-137 for 6 hours or 10 ng/ml TNF for 2 hours as a positive control is shown.

FIG. 2F shows the effect of curaxin-137 treatment on p53 protein levels in normal mammary cells and mammary tumor cells from MMTV-neu mice. Western blotting of protein extracts of cells isolated from tumor free mammary gland and several different tumors of two mice. Cells were left untreated (−) or treated ex vivo with increasing concentrations of curaxin-137 (1-10 μM) for 6 h. Based on the difference between basal and induced level of p53 protein p53 pathway in cells was proposed, without wishing to be bound by theory: (+)-active (p53 is most probably wild type), (−)-non active (p53 is most probably mutated).

FIGS. 3A-3E show the safety of chronic administration of curaxin-137 with drinking water. FIGS. 3A-3E show groups of MMTV-neu mice (n=5/group) which were given regular water (control) or solutions of curaxin-137 (0.1 or 0.2 mg/ml) ad libitum from 4 to 14 weeks of age.

FIG. 3A shows that the rate of liquid consumption by MMTV-mice was similar for groups given regular water or solutions of curaxin-137 (0.1 or 0.2 mg/ml). Y-axis calculated amount consumed by every mouse in a cage per day based on weighting bottles once a week.

FIG. 3B shows the actual dose of curaxin-137 delivered with drinking water. The average daily dose of curaxin-137 was calculated using measurements from A and C.

FIG. 3C shows curaxin-treated and control mice gained weight at similar rates. The average body weight of mice in the three study groups is shown normalized to the average weight for each group at 4 weeks of age. Error bars indicate standard deviation between 5 mice per group.

FIG. 3D shows Kaplan-Meier survival curves illustrating non-tumor-related mortality of MMTV-neu animals in the three study groups. 0.1 mg/ml group started treatment at 4 weeks of age and 0.2 mg/ml at 10 weeks of age. No tumors were visible or palpable in mice that died before 44 weeks of age. Data were analyzed using MedCalc v.11.3.3 and survival curves were compared using Log-rank test, p>0.1 for each curaxin-treated group versus the control group.

FIG. 3E shows hierarchical clustering analysis of gene expression profiles of samples isolated from 2 mice in each treatment group, control (plain water), and treated 0.1 and 0.2 mg/ml of curaxin-137 from 4 to 14 weeks of age. Liver and spleen RNAs were analyzed.

FIGS. 4A-4C show an absence of morphological changes in organs of MMTV-neu mice treated with curaxin-137 from 4 to 14 weeks of age. 5 animals per group were subjected to blind histopathological analysis. H&E-stained sections were prepared from most organs.

FIG. 4A shows bone marrow samples (first column) of the three groups of mice showed densely packed hematopoietic cells of all lineages and various maturities, indicating active hematopoiesis. Spleen samples of mice of all groups (columns 2 and 3) had normal morphology with lymphoid cells in the white pulp and active hematopoiesis in the red pulp.

FIG. 4B shows the morphology of the liver (first column), lung (second column) and kidney (third column) Liver histology was normal in all mice with more compact cytoplasm of the periportal hepatocytes and more vacuolar cytoplasm of the cells around the terminal vein of the lobules. All mice also showed normal lung (alveoli, bronchioles and blood vessels) and kidney (glomeruli and tubules) histology.

FIG. 4C shows morphology of the gastrointestinal tract. Normal morphology of the samples from the intestines of all mice with unaltered surface epithelium, villi, lamina propria, crypts and mucosa associated lymphoid tissue FIGS. 5A-5C show the effect of chronic administration of curaxin-137 on overall and tumor-free survival of female MMTV-neu transgenic mice.

FIG. 5A shows that curaxin-137 (here, CBL 137) prolonged overall survival of mice in a dose-dependent manner. Kaplan-Meier survival curves are shown for each group of animals (control—regular drinking water, or 0.1 or 0.2 mg/ml curaxin-137 (CBLC137) in drinking water from 4 to 14 weeks of age; n=19-25/group). Data were analyzed using MedCalc v.11.3.3 and survival curves were compared using the Log-rank test; p<0.0001 for both treatment groups.

FIG. 5B shows tumor onset (appearance of visible tumors) was delayed in animals treated with curaxin-137 (CBL 137) in a dose-dependent manner Kaplan-Meier curves of tumor-free survival were generated for the groups described in A and were analyzed as in A; p<0.001 for both treatment groups.

FIG. 5C shows tumor multiplicity in three groups of mice shown as average number of tumors of different size category (big, medium, small) in mice determined upon necropsy. Error bars—standard deviation between 19-25 animals analyzed per each group. Asterisks show statistically significant difference from untreated animals (t-test, p<0.05).

FIGS. 6A-6G show an analysis of histological types of mammary tumors observed in control and curaxin-137-treated female MMTV-neu mice. FIGS. 6A-6F show microphotographs of H&E-stained sections of mouse mammary tumors of different histological subtypes:

FIG. 6A: "undifferentiated;"

FIG. 6B: "low grade" with poorly differentiated; glandular-like structures;

FIG. 6C: thick tubular structures;

FIG. 6D: "glandular;"

FIG. 6E: carcinoma in situ; and

FIG. 6F hyperplastic mammary epithelia.

FIG. 6G shows the proportion of tumors of different types (A-F) among experimental groups. P values demonstrates significance of difference in the number of tumors of different histological types between treated and control animals according to Chi-square test.

Figure 7:
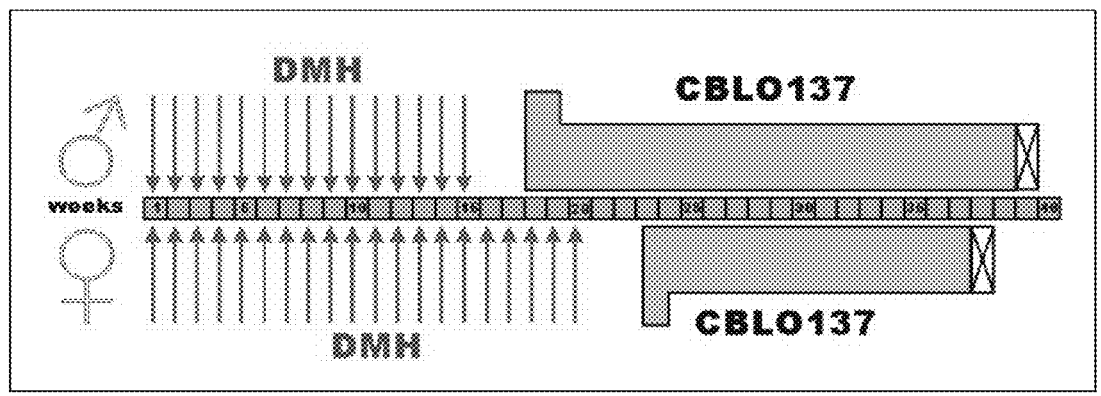

FIG. 7 shows the experimental design of the DMH study.

Figure 8:
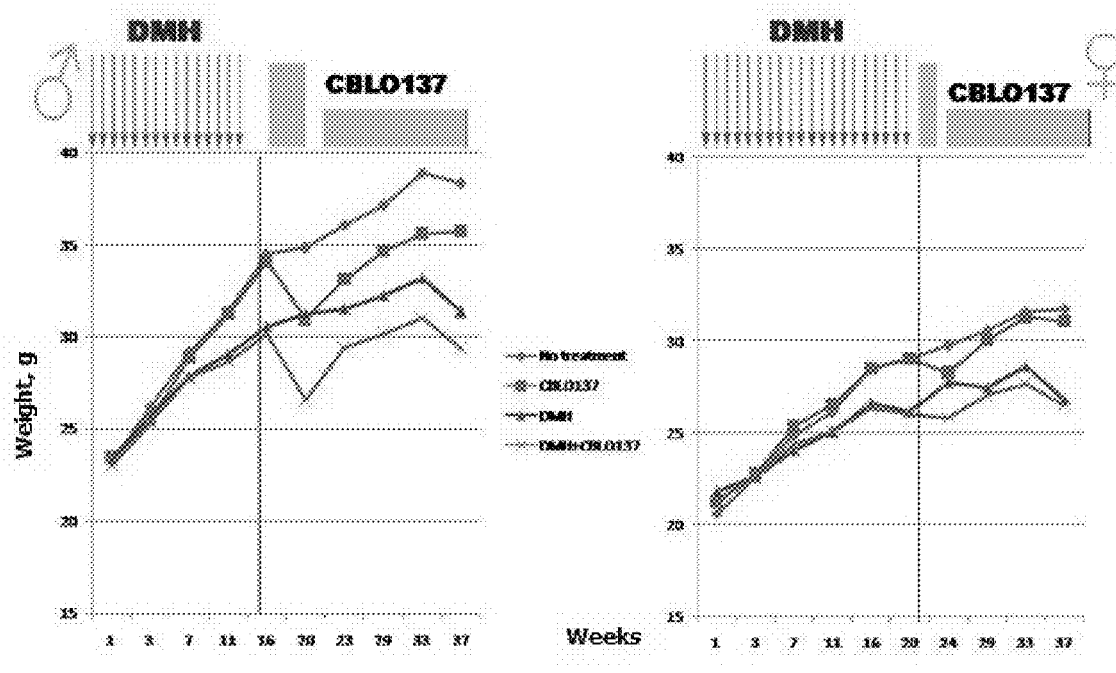

FIG. 8 shows the dynamic changes in mice bodyweight throughout the DMH study.

FIG. 9 shows the concentration of curaxin-137 (μM) in mouse plasma and tissues (mean+/−SD in μM, n=4) 10 weeks after start of treatment (14 weeks of age).

FIG. 10 shows histopathological findings in old animals in each treatment group (2 mice per group).

FIG. 11 shows the incidence rate of tumors, induced by DMH in female mice.

FIG. 12 shows the incidence rate of tumors, induced by DMH in male mice.

FIG. 13 shows the weight of organs extracted during the necropsy from female animals in the DMH study.

FIG. 14 shows the weight of organs extracted during the necropsy from male animals in the DMH study.

FIG. 15 shows macroscopic changes in organs of female mice.

FIG. 16 shows macroscopic changes in organs of male mice.

DETAILED DESCRIPTION OF THE INVENTION

The present invention is based, in part, on the discovery that curaxins have an anti-cancer effect in cancers, specifically breast cancers that are characterized by certain molecular markers, including but not limited to ER, PR, HER2, and FACT.

In one aspect, the present invention provides a method for treating breast cancer in a subject in need thereof comprising administering an effective amount of a compound of Formula I:

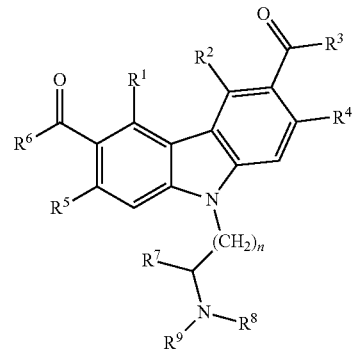

wherein each of $R^1$—$R^9$ are independently H, hydroxyl or alkyl; n is 0, 1, 2, 3, 4, or 5; or a pharmaceutically acceptable salt or hydrate thereof; and the breast cancer is one or more of estrogen receptor positive ($ER^+$), human epidermal growth factor receptor 2 positive ($HER2^+$), progesterone receptor positive (PR+), and facilitates chromatin transcription positive (FACT).

In some embodiments the compound of Formula I is curaxin 137, which is:

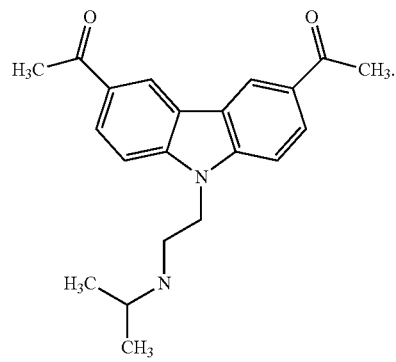 [SMILES: CC(=O)c1ccc2c(c1)c1cc(C(C)=O)ccc1n2CCNC(C)C]

In some embodiments the breast cancer is $ER^+$, or $HER2^+$, or $FACT^+$, or $PR^+$, or $ER^+$ and $HER2^+$, or $ER^+$ and $FACT^+$, or $ER^+$ and $PR^+$, or $HER2^+$ and $FACT^+$, or $HER2^+$ and $PR^+$, or $FACT^+$ and $PR^+$, or $ER^+$ and $HER2^+$ and $FACT^+$, or $ER^+$ and $HER2^+$ and $PR^+$, or $ER^+$ and $FACT^+$ and $PR^+$, or $HER2^+$ and $FACT^+$ and $PR^+$, or $ER^+$ and $HER2^+$ and $FACT^+$ and $PR^+$.

In some embodiments the compound of Formula I is administered in combination with an additional cancer therapy, such as, for example, hormone therapy.

In various embodiments, the subject does not receive hormone therapy or hormone therapy was ineffective.

In various embodiments, the compound of Formula I is administered as an adjuvant therapy after resection, including, without limitation, as the sole adjuvant therapy.

In some embodiments the compound of Formula I is administered as a neoadjuvant therapy prior to resection.

In various embodiments, the subject is a human, for example, a female human.

In various embodiments, the breast cancer is resistant to platinum drugs and/or taxanes, or is determined to be resistant to platinum drugs or taxanes based on a chemosensitivity test or surrogate biomarker.

In another aspect, the present invention provides a method for identifying a subject who has a breast cancer tumor and is likely not to respond to treatment with a compound of Formula I, comprising evaluating the tumor comprising measuring a presence, absence, or level of at least one of ER, PR, HER2, and FACT; wherein the presence of at least one of ER, PR, HER2, and FACT indicates that the subject is likely to respond to treatment with a compound of Formula I and wherein the compound of Formula I is:

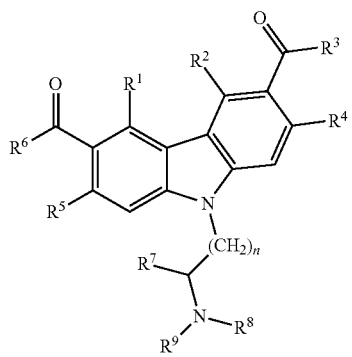

(I)

wherein each of R$^1$—R$^9$ are independently H, hydroxyl or alkyl and n is 0, 1, 2, 3, 4, or 5; or a pharmaceutically acceptable salt or hydrate thereof.

In some embodiments, the method for identifying a subject who has a breast cancer tumor and is likely to respond to treatment with a compound of Formula I further comprises administering an effective amount of the compound of Formula I or a pharmaceutically acceptable salt thereof to a subject that is likely to respond to the compound of Formula I.

In some embodiments, the compound of Formula I is:

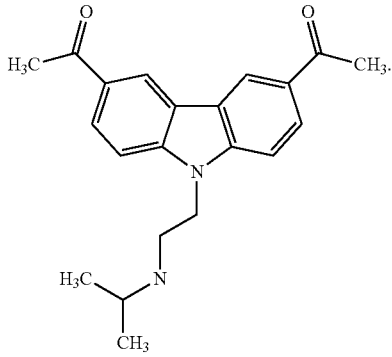 [SMILES: CC(=O)c1ccc2c(c1)c1cc(C(C)=O)ccc1n2CCNC(C)C]

In various embodiments, the measurement comprises evaluating a presence, absence, or level of a protein.

In still other embodiments, the measurement comprises contacting a specimen of the tumor or cells cultured from the tumor with an agent that specifically binds at least one of ER, PR, HER2, and FACT. In some embodiments, the agent that specifically binds at least one of ER, PR, HER2, and FACT is an antibody.

In still other embodiments, the measurement of at least one of ER, PR, HER2, and FACT comprises one or more of immunohistochemical staining, western blotting, in cell western, immunofluorescent staining, ELISA, and fluorescent activating cell sorting (FACS).

In other embodiments, the tumor specimen is a biopsy selected from a frozen tumor tissue specimen, cultured cells, circulating tumor cells, and a formalin-fixed paraffin-embedded tumor tissue specimen.

The following definitions are used in connection with the invention disclosed herein. Unless defined otherwise, all technical and scientific terms used herein have the same meaning as commonly understood to one of skill in the art to which this invention belongs.

As used herein, "a," "an," or "the" can mean one or more than one. Further, the term "about" when used in connection with a referenced numeric indication means the referenced numeric indication plus or minus up to 10% of that referenced numeric indication. For example, the language "about 50" covers the range of 45 to 55.

The term "administer", "administering", or "administration" as used in this disclosure refers to either directly administering a compound or pharmaceutically acceptable salt of the compound or a composition to a subject, or administering a prodrug conjugate or analog of the compound or pharmaceutically acceptable salt of the compound or composition to the subject, which can form an equivalent amount of active compound within the subject's body.

The term "alkyl," as used herein unless otherwise defined, refers to a straight or branched saturated group derived form the removal of a hydrogen atom from an alkane. Representative straight chain alkyl groups include, but are not limited to, -methyl, -ethyl, -n-propyl, -n-butyl, -n-pentyl, and n-hexyl. Representative branched alkyl groups include, but are not limited to, isopropyl, -sec-butyl, -isobutyl, -tert-butyl, -isopentyl, -neopentyl, 1-methylbutyl, 2-methylbutyl, 3-methylbutyl, 1,1-dimethylpropyl and 1,2-dimethylpropyl.

The term "carrier", as used in this disclosure, encompasses carriers, excipients, and diluents and means a material, composition or vehicle, such as a liquid or solid filler, diluent, excipient, solvent or encapsulating material, involved in carrying or transporting a pharmaceutical agent from one organ, or portion of the body, to another organ, or portion of the body.

Although the open-ended term "comprising," as a synonym of terms such as including, containing, or having, is used herein to describe and claim the invention, the present invention, or embodiments thereof, may alternatively be described using alternative terms such as "consisting of" or "consisting essentially of."

The term "disorder" is used in this disclosure to mean, and is used interchangeably with, the terms disease, condition, or illness, unless otherwise indicated.

An "effective amount," when used in connection with a compound described herein is an amount that is effective for providing a measurable treatment, prevention, or reduction in the pathogenesis of a cancer or related disease such as, for example, breast cancer.

"Hormone therapy" is an anti-cancer therapy that may involve a manipulation of the endocrine system. This therapy may comprise drugs which inhibit the production or activity of hormones (hormone antagonists), for example.

"Hormone therapy" is an anti-cancer therapy that may involve a manipulation of the endocrine system. This therapy may comprise drugs which inhibit the production or activity of hormones (hormone antagonists), for example.

The term "hydroxyl" means —OH.

A "subject" is a mammal, e.g., a human (e.g. a female or a male human), mouse, rat, guinea pig, dog, cat, horse, cow, pig, or non-human primate, such as a monkey, chimpanzee, baboon or rhesus, and the terms "subject" and "patient" are used interchangeably herein.

The term "treating", with regard to a subject, refers to improving at least one symptom of the subject's disorder. Treating can be curing, improving, or at least partially ameliorating the disorder, including cancer or a related disease such as, for example, breast cancer. Treatment can be assessed using various endpoints, including overall survival, progression-free interval, disease-free interval, or pathological complete response.

As referred to herein, all compositional percentages are by weight of the total composition, unless otherwise specified. As used herein, the word "include," and its variants, is intended to be non-limiting, such that recitation of items in a list is not to the exclusion of other like items that may also be useful in the materials, compositions, devices, and methods of this technology. Similarly, the terms "can" and "may" and their variants are intended to be non-limiting, such that recitation that an embodiment can or may comprise certain elements or features does not exclude other embodiments of the present technology that do not contain those elements or features.

In general, compositions of the invention include a carbazole compound. Suitable carbazole compounds and methods of making them are described in PCT/US2009/059558, filed Oct. 5, 2009, the entire disclosure of which is incorporated herein by reference. In certain embodiments, the carbazole is a compound referred to herein as a curaxin.

In various embodiments, the present invention relates to a compound of Formula I:

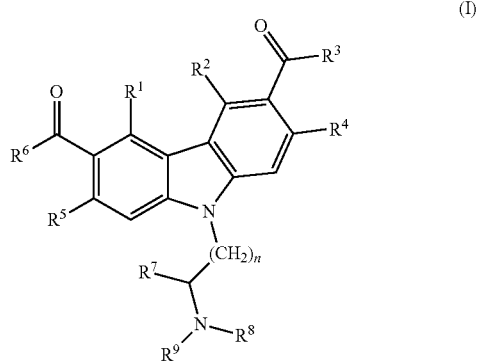

wherein each of $R^1$—$R^9$ are independently H, hydroxyl or alkyl;

n is 0, 1, 2, 3, 4, or 5;

or a pharmaceutically acceptable salt or hydrate thereof.

In various embodiments, a compound of Formula I or a pharmaceutically acceptable salt or hydrate thereof is referred to herein as a curaxin.

Curaxins combine two groups of chemical compounds with different structures but with similar molecular mechanism of action on tumor cells. The first group includes derivatives of 9-aminoacridine (including, e.g., the antimalarial drug Acrichine). The second group includes compounds that have a carbazole nucleus. In some embodiments, the carbazole structure can comprise acetyl and/or alkylacyl and/or alkyl ketone substituents. In some embodiments, side chain(s) attached to the carbazole nitrogen atom can comprise a linear or branched alkylamine and may contain secondary and tertiary amino groups.

In one embodiment, the compound has the structure:

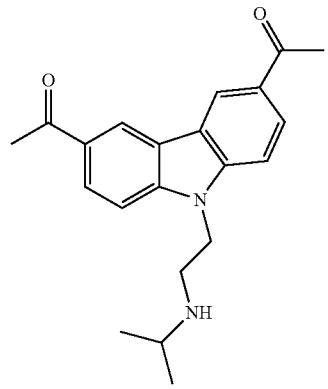

The compound above is referred to generally as a curaxin and specifically referred to herein as curaxin-137 and/or CBL-137 and/or CBL0137.

In various embodiments, the present invention relates to cancer. In some embodiments, the invention pertains to breast cancer. In some embodiments, the invention relates to specific subtypes of breast cancer, including, but not limited to $ER^+$, or $HER2^+$, or $FACT^+$, or $PR^+$, or $ER^+$ and $HER2^+$, or $ER^+$ and $FACT^+$, or $ER^+$ and $PR^+$, or $HER2^+$ and $FACT^+$, or $HER2^+$ and $PR^+$, or $FACT^+$ and $PR^+$, or $ER^+$ and $HER2^+$ and $FACT^+$, or $ER^+$ and $HER2^+$ and $PR^+$, or $ER^+$ and $FACT^+$ and $PR^+$, or $HER2^+$ and $FACT^+$ and $PR^+$, or $ER^+$ and $HER2^+$ and $FACT^+$ and $PR^+$. In some embodiments, the invention relates to specific subtypes of breast cancer, including, but not limited to $ER^-$, or $HER2^-$, or $FACT^-$, or $PR^-$, or $ER^-$ and $HER2^-$, or $ER^-$ and $FACT^-$, or $ER^-$ and $PR^-$, or $HER2^-$ and $FACT^-$, or $HER2^-$ and $PR^-$, or $FACT$ and $PR^-$, or $ER^-$ and $HER2^-$ and $FACT^-$, or $ER^-$ and $HER2^-$ and $PR^-$, or $ER^-$ and $FACT$ and $PR^-$, or $HER2^-$ and $FACT$ and $PR^-$, or $ER^-$ and $HER2^-$ and $FACT$ and $PR^-$.

A cancer or tumor refers to an uncontrolled growth of cells and/or abnormal increased cell survival and/or inhibition of apoptosis which interferes with the normal functioning of the bodily organs and systems. A subject that has a cancer or a tumor is a subject having objectively measurable cancer cells present in the subject's body. Included in this invention are benign and malignant cancers, as well as dormant tumors or micrometastatses. Cancers which migrate from their original location and seed vital organs can eventually lead to the death of the subject through the functional deterioration of the affected organs.

In various embodiments, the invention is applicable to pre-metastatic cancer, or metastatic cancer. Metastasis refers to the spread of cancer from its primary site to other places in the body. Cancer cells can break away from a primary tumor, penetrate into lymphatic and blood vessels, circulate through the bloodstream, and grow in a distant focus (metastasize) in normal tissues elsewhere in the body. Metastasis can be local or distant. Metastasis is a sequential process, contingent on tumor cells breaking off from the primary tumor, traveling through the bloodstream, and stopping at a distant site. At the new site, the cells establish a blood supply and can grow to form a life-threatening mass. Both stimulatory and inhibitory molecular pathways within the tumor cell regulate this behavior, and interactions between the tumor cell and host cells in the distant site are also significant.

Metastases are often detected through the sole or combined use of magnetic resonance imaging (MRI) scans, computed tomography (CT) scans, blood and platelet counts, liver function studies, chest X-rays and bone scans in addition to the monitoring of specific symptoms.

The methods and compositions described herein are directed toward the treatment of cancer, and/or the treatment, prevention or amelioration of growth, progression, and/or metastases of malignancies and proliferative disorders associated with increased cell survival, or the inhibition of apoptosis. In some embodiments, the invention pertains to breast cancer.

Breast cancer is a type of cancer originating from breast tissue, including the inner lining of milk ducts (ductal carcinomas) or the lobules that supply the ducts with milk (lobular carcinomas). Breast cancer occurs in humans and other mammals. Most human cases occur in women, male breast cancer can also occur. In some embodiments, the present invention pertains to a female human breast cancer subject. In some embodiments, the present invention pertains to a male human breast cancer subject.

Breast cancers may be classified by one or more grading systems, which may, influence the prognosis and can affect treatment response. Histopathology, describes the classification of breast cancer by its histological appearance. Most breast cancers are derived from the epithelium lining the ducts or lobules, and these cancers are classified as ductal or lobular carcinoma. Carcinoma in situ is growth of low grade cancerous or precancerous cells within a particular tissue compartment such as the mammary duct without invasion of the surrounding tissue. By contrast, invasive carcinoma does not confine itself to the initial tissue compartment. Grading compares the appearance of breast cancer cells to the appearance of normal breast tissue. In some embodiments, cancerous cells lose the differentiation and orderly arrangement that characterizes normal cells and normal populations of cells. Further, cell division may become uncontrolled and cell nuclei may become less uniform. Cells can be binned as well differentiated (low grade), moderately differentiated (intermediate grade), and poorly differentiated (high grade) as the cells progressively lose the features seen in normal breast cells. Poorly differentiated cancers (the ones whose tissue is least like normal breast tissue) have a worse prognosis. Breast cancer staging can be undertaken using the TNM system, which is based the size of the tumor (T), whether or not the tumor has spread to the lymph nodes (N) in the armpits, and whether the tumor has metastasized (M). Larger size, nodal spread, and metastasis have a larger stage number and a worse prognosis. The main stages are: stage 0 is a pre-cancerous or marker condition, either ductal carcinoma in situ (DCIS) or lobular carcinoma in situ (LCIS); stages 1-3 are within the breast or regional lymph nodes; and stage 4 is metastatic cancer that often has a less favorable prognosis. DNA testing of various types including DNA microarrays may also be used to compare normal cells to breast cancer cells. The specific changes in a particular breast cancer can be used to classify the cancer in several ways, and may assist in choosing the most effective treatment for that DNA type.

Further, receptor status is important for classifying cancers, and the receptor status can be important for determining the optimum course of treatment. Breast cancer cells have receptors on their surface and in their cytoplasm and nucleus. Chemical messengers such as hormones bind to receptors, and this causes changes in the cell. Breast cancer cells may or may not have at least three important receptors: estrogen receptor (ER), progesterone receptor (PR), and HER2, as described herein.

In some embodiments, the invention relates to specific subtypes of breast cancer, including, but not limited to $ER^+$, or $HER2^+$, or $FACT^+$, or $PR^+$, or $ER^+$ and $HER2^+$, or $ER^+$ and $FACT^+$, or $ER^+$ and $PR^+$, or $HER2^+$ and $FACT^+$, or $HER2^+$ and $PR^+$, or $FACT^+$ and $PR^+$, or $ER^+$ and $HER2^+$ and $FACT^+$, or $ER^+$ and $HER2^+$ and $PR^+$, or $ER^+$ and $FACT^+$ and $PR^+$, or $HER2^+$ and $FACT^+$ and $PR^+$, or $ER^+$ and $HER2^+$ and $FACT^+$ and $PR^+$. In some embodiments, the invention relates to specific subtypes of breast cancer, including, but not limited to $ER^-$, or $HER2^-$, or $FACT^-$, or $PR^-$, or $ER^-$ and $HER2^-$, or $ER^-$ and FACT, or $ER^-$ and $PR^-$, or $HER2^-$ and FACT, or $HER2^-$ and $PR^-$, or FACT and $PR^-$, or $ER^-$ and $HER2^-$ and FACT, or $ER^-$ and $HER2^-$ and $PR^-$, or $ER^-$ and FACT and $PR^-$, or $HER2^-$ and FACT and $PR^-$, or $ER^-$ and $HER2^-$ and FACT and $PR^-$.

Further, in some embodiments, the invention relates to specific subtypes of breast cancer, including, any of the combinations above along with the presence or absence of additional receptors, such as, for example, the androgen receptor (AR) and the prolactin receptor (PRLr). Accordingly, in some embodiments, the specific subtypes of breast cancer of the invention are at least androgen receptor positive ($AR^+$) or androgen receptor negative ($AR^-$). Accordingly, in some embodiments, the specific subtypes of breast cancer of the invention are at least prolactin receptor positive ($PRLr^+$) or prolactin receptor negative ($PRLr^-$).

Although the etiological mechanism underlying breast cancer is not fully understood, hormones play a significant role in almost 70% of cases and many current treatment strategies have targeted hormonally responsive breast cancers. These breast cancers are "ER-positive" ($ER^+$) and can be demonstrated in such tissues using immunohistochemistry, or any of the other techniques known in the art and/or described herein.

Estrogen is a promoter of cell division in the breast, where it causes proliferation of both normal and malignant cells. The two major classes of antiestrogenic drugs, the selective estrogen receptor modulators (SERMs) and the aromatase inhibitors (AIs), have been recently used for their activity in breast cancer treatment. In some embodiments, tamoxifen is a relevant antiestrogenic drug of the invention.

Estrogens have been shown to play an important role in the modulation of estrogen receptor positive breast carcinoma. Binding of endogenous estrogens, in particular 17β-estradiol ($E_2$), to the estrogen receptor has been linked to proliferation of the carcinoma cells by, without wishing to be bound by theory, causing the carcinoma cells to shift from the $G_1$ phase of the cell cycle to the S phase of the cell cycle. The $G_1$ stage of interphase is characterized by the cell being in a resting state, whereas it is during the S phase that the DNA synthesis necessary for cell survival and proliferation occurs. Without wishing to be bound by theory, this binding of estrogen to the ER which stimulates proliferation of mammary cells, with the resulting increase in cell division and DNA replication, may lead to tumorigenic mutations. Additionally, and also without wishing to be bound by theory, ER may be linked to breast cancer by the effects of estrogen metabolism, which produces genotoxic waste.

Estrogen receptors are a group of proteins that are activated by the hormone estrogen (17β-estradiol). At least two classes of estrogen receptor exist: ER, which is a member of the nuclear hormone family of intracellular receptors, and GPER, which is a member of the rhodopsin-like family of G protein-coupled receptors. Once activated by estrogen, ER is able to operate like a transcription factor and translocate into the nucleus and bind to DNA to regulate the activity of different genes. Addition, a small pool of ERs localizes to the plasma membrane and signals mainly though coupling, directly or indirectly, to G proteins. In response to steroid, signal transduction modulates both nontranscriptional and transcriptional events and impacts both the rapid and more prolonged actions of estrogen.

One current trend in the treatment of estrogen receptor positive breast carcinoma is the use of anti-estrogenic agents that prevent the binding of $E_2$ to the estrogen receptor. It has been postulated that an anti-estrogen may inhibit $E_2$ binding through competitive inhibition at the estrogen receptor or alternatively by binding to another site such as the anti-estrogen or calmodulin receptor, thereby preventing the binding of $E_2$ to the estrogen receptor (Pharmacol Rev 36: 245 (1984)). In one study, approximately 60% of patients with estrogen receptor positive breast cancer (>10 femtomol/mg cytosol protein) responded to anti-estrogen therapy, whereas less than 10% of patients with estrogen receptor negative tumors (<10 femtomol/mg cytosol protein) responded. (see J. L. Borgna, Biochem Pharmacol 31: 3187 (1982)).

Regardless of the approach, $ER^+$ breast cancer, a type of breast cancer that is sensitive to estrogen, which stimulates tumor growth, can show different levels of responsiveness to conventional therapies, as compared to $ER^-$ breast tumors.

In some embodiments, aggressiveness of a tumor is determined by using one or more of three measurements from a pathology report: cell differentiation, mitotic activity, and cell nuclei abnormality. Information about these measurements usually is provided through three scales that are totaled to give a score that ranges from three to nine. In the cell differentiation assessment, "normal" breast cell differentiation means that the cells are able to normally form the glands that make up the breast tissue. When cells form tissue that looks less like breast tissue glands, they are called less differentiated. This usually is a sign of a more aggressive cancer. Scores generally range from one to three, with higher scores indicating less differentiation. In the mitotic activity assessment, a measure of fast the tumor cells are dividing. Aggressive tumors have a large number of cells in the act of dividing (mitosis). Scores range from one to three, with higher scores indicating more aggressive activity. In the cell nuclei abnormality assessment, the nuclei of the cells are graded based on how similar in size they appear. Scores range from one to three, with higher scores indicating higher levels of lumpy, differently sized nuclei. Often the these three assessments are taken as a sum to scale aggressiveness: a score of three to five out of nine is called grade one, and tends to indicate a less aggressive cancer; a score of six to seven is grade two, and a score of eight to nine is grade three, and tends to indicate a more aggressive cancer. In some embodiments, other measurements known in the art may be used to assess aggressiveness of a cancer.

Accordingly, the present invention, inter alia, pertains to the use of the compounds described herein to treat $ER^+$ cancer. In some embodiments, the $ER^+$ cancer is breast cancer. In some embodiments, the $ER^+$ cancer is a particular subtype of breast cancer and may be in the context of other biomarkers (e.g. FACT and/or PR and/or HER2).

In some embodiments, the $ER^+$ cancer is one or more of ovarian cancer, colon cancer, prostate cancer, endometrial cancer, stomach cancer, and uterine cancer. In some embodiments, the $ER^+$ cancer is a particular subtype of ovarian cancer and/or colon cancer and/or prostate cancer and/or endometrial cancer and/or stomach and/or uterine cancer and may be in the context of other biomarkers (e.g. FACT and/or PR and/or HER2). In some embodiments, the colon cancer is associated with a loss of ERβ, the predominant ER in colon tissue, and colon cancer is treated with ERβ-specific agonists.

HER2 (also known as Neu, ErbB-2, CD340, or p185) is a protein that in humans is encoded by the ERBB2 gene, a known proto-oncogene. HER2 is a member of the epidermal growth factor receptor (EGFR/ErbB) family. Amplification or over-expression of this gene has been shown to play an important role in the pathogenesis and progression of certain aggressive types of cancer, including breast cancer.

Without wishing to be bound by theory, signaling pathways activated by HER2 include, but are not limited to, mitogen-activated protein kinase (MAPK), phosphoinositide 3-kinase (PI3K/Akt), phospholipase C γ, protein kinase C (PKC), and signal transducer and activator of transcription (STAT).

Generally, signaling through the ErbB family of receptors promotes cell proliferation and opposes apoptosis. Amplification or over-expression of the ERBB2 gene occurs in approximately 30% of breast cancers. It is strongly associated with increased disease recurrence and a worse prognosis. Accordingly, HER2+ breast cancer is a particularly aggressive subtype of breast cancer and often has a bad prognosis.

The present invention, inter alia, pertains to the use of the compounds described herein to treat $HER2^+$ cancer. In some embodiments, $HER2^+$ cancer can be demonstrated in such tissues using immunohistochemistry, or any of the other techniques known in the art and/or described herein. In some embodiments, the $HER2^+$ cancer is breast cancer. In some embodiments, the $FACT^+$ cancer is a particular subtype of breast cancer and may be in the context of other biomarkers (e.g. PR and/or ER and/or FACT).

In some embodiments, the $HER2^+$ cancer is one or more of ovarian cancer, colon cancer, prostate cancer, endometrial cancer, stomach cancer, and uterine cancer. In some embodiments, the $HER2^+$ cancer is a particular subtype of ovarian cancer and/or colon cancer and/or prostate cancer and/or endometrial cancer and/or stomach and/or uterine cancer and may be in the context of other biomarkers (e.g. PR and/or ER and/or FACT).

Progesterone is a major regulator of breast epithelial cell proliferation and differentiation. Progesterone is a fundamental controller of breast development and function. But, exposure to progesterone can increase the chance of developing breast cancer, including when used after menopause together with estrogens.

The progesterone receptor is a progestin-activated steroid receptor member of the nuclear receptor superfamily of transcription factors. It plays a central role in diverse reproductive events associated with establishment and maintenance of pregnancy, alveolar development in the breast and sexual behavior. Genetically modified animals lacking PR ($PR^-$) have a significantly lower incidence of mammary tumors compared with wild-type mice. Clinical and experimental evidence suggests that progesterone exposure may have a role in facilitating metastasis of $PR^+$ breast cancers to lymph nodes and distant organs, which is a main cause of morbidity and death due to this disease.

Without wishing to be bound by theory, progesterone may enhance the invasiveness of breast cancer cells by, at least, increasing tissue factor or vascular endothelial growth factor expression, or augmenting matrix metalloproteinases and urokinase-type plasminogen activator activities, or triggering the formation of focal adhesion (FA) complexes, which provide anchoring sites for cell attachment to the extracellular matrix during cell movement and invasion.

Regardless of the mechanism, $PR^+$ breast cancer, a type of breast cancer that is sensitive to progesterone, which stimulates tumor growth, and $PR^+$ breast cancers may be responsive to different treatments than $PR^-$ cancers. In some embodiments, $PR2^+$ cancer can be demonstrated in such tissues using immunohistochemistry, or any of the other techniques known in the art and/or described herein.

Accordingly, the present invention, inter alia, pertains to the use of the compounds described herein to treat PR$^+$ cancer. In some embodiments, the PR$^+$ cancer is breast cancer. In some embodiments, the PR$^+$ cancer is a particular subtype of breast cancer and may be in the context of other biomarkers (e.g. FACT and/or ER and/or HER2).

In some embodiments, the PR$^+$ cancer is one or more of ovarian cancer, colon cancer, prostate cancer, endometrial cancer, stomach cancer, and uterine cancer. In some embodiments, the PR$^+$ cancer is a particular subtype of ovarian cancer and/or colon cancer and/or prostate cancer and/or endometrial cancer and/or stomach and/or uterine cancer and may be in the context of other biomarkers (e.g. FACT and/or PR and/or HER2).

The FAcilitates Chromatin Transcription (FACT) complex is a heterodimer of two subunits: an 80 kDa subunit and a 140 kDa subunit. These subunits are Structure Specific Recognition Protein 1 (SSRP1) and Suppressor of Ty (SPT16 or SUPT16H). As used herein, FACT refers to the heterodimer of SSRP1 and SPT16, or the individual SSRP1 and SPT16 subunits. Without wishing to be bound by theory, FACT is involved in chromatin remodeling through modulating of nucleosome stability. FACT may be involved in many processes involving chromatin, such as, for example, transcription, replication, recombination, DNA damage, and repair. FACT interacts specifically with histones H2A/H2B to effect nucleosome disassembly and transcription elongation. Curaxins (e.g. Curaxin-137), small molecules which have broad anti-cancer activity in different models of cancer (See International Patent Publication No. WO 2010/042445, the contents of which are hereby incorporated by reference in their entirety), cause functional inactivation of FACT (See Gasparian, et al. Sci. Trans. Med. 3: 95ra74 (2011), the contents of which are hereby incorporated by reference in their entirety).

The protein encoded by the gene of structure specific recognition protein 1 (SSRP1) (mRNA in humans: NM_003146.2, the sequence is hereby incorporated by reference in its entirety, mRNA in mouse: NM_001136081.1, the sequence is hereby incorporated by reference in its entirety) is a subunit of a heterodimer that, along with SPT16, forms FACT. SSRP1 is the 80 kDa subunit. FACT and cisplatin-damaged DNA may be crucial to the anticancer mechanism of cisplatin. SSRP1 encoded protein (in humans: NP_003137.1, the sequence is hereby incorporated by reference in its entirety, in mouse: NP_001129553.1, the sequence is hereby incorporated by reference in its entirety) contains a high mobility group box which, without wishing to be bound by theory, may constitutes the structure recognition element for cisplatin-modified DNA. SSRP1 is also a component of a CK2-SPT16-SSRP1 complex which forms following UV irradiation, comprising SSRP1, SUPT16H, CSNK2A1, CSNK2A2 and CSNK2B. SSRP1 has been shown to interact with NEK9, a serine/threonine-protein kinase. SSRP1 protein also functions as a co-activator of the transcriptional activator p63 (including, for example, isoform gamma of TP63). SSRP1 enhances the activity of full-length p63, but it has no effect on the N-terminus-deleted p63 (DeltaN-p63) variant. SSRP1 also interacts with FYTTD1/UIF and SRF.

SPT16 (SUPT16H) is a protein that in humans is encoded by the SUPT16H gene (mRNA in humans: NM_007192.3, the sequence is hereby incorporated by reference in its entirety, mRNA in mouse: NM 033618.3, the sequence is hereby incorporated by reference in its entirety). The SPT16 protein (in humans: NP_009123.1, the sequence is hereby incorporated by reference in its entirety, in mouse: NP_291096.2, the sequence is hereby incorporated by reference in its entirety) is the 140 kDa subunit in the FACT complex. SPT16 is also a component of a CK2-SPT16-SSRP1 complex which forms following UV irradiation, comprising SSRP1, SUPT16H, CSNK2A1, CSNK2A2 and CSNK2B. Additionally, SPT16 is a component of the WINAC complex, comprising, at least, SMARCA2, SMARCA4, SMARCB1, SMARCC1, SMARCC2, SMARCD1, SMARCE1, ACTL6A, BAZ1B/WSTF, ARID1A, SUPT16H, CHAF1A and TOP2B. SPT16 has been shown to interact with BAZ1B, a tyrosine-protein kinase. SPT16 also interacts with NEK9, general transcription factor IIE subunit 2 (GTF2E2), and binds to histone H2A-H2B.

FACT has been linked to aggressive cancers of many varieties. See U.S. Provisional Application No. 61/763,266, filed Feb. 11, 2013, the contents of which are hereby incorporated by reference herein in their entirety.

Accordingly, the present invention, inter alia, pertains to the use of the compounds described herein to treat FACT$^+$ cancer. In some embodiments, the FACT$^+$ cancer is breast cancer. In some embodiments, the FACT$^+$ cancer is a particular subtype of breast cancer and may be in the context of other biomarkers (e.g. PR and/or ER and/or HER2). In some embodiments, FACT$^+$ cancer can be demonstrated in such tissues using immunohistochemistry, or any of the other techniques known in the art and/or described herein.

In some embodiments, the FACT$^+$ cancer is one or more of ovarian cancer, colon cancer, prostate cancer, endometrial cancer, stomach cancer, and uterine cancer. In some embodiments, the FACT$^+$ cancer is a particular subtype of ovarian cancer and/or colon cancer and/or prostate cancer and/or endometrial cancer and/or stomach and/or uterine cancer and may be in the context of other biomarkers (e.g. PR and/or ER and/or HER2).

A breast cancer can be classified as a certain subtype (e.g. ER$^+$, or HER2$^+$, or FACT$^+$, or PR$^+$, or ER$^+$ and HER2$^+$, or ER$^+$ and FACT$^+$, or ER$^+$ and PR$^+$, or HER2$^+$ and FACT$^+$, or HER2$^+$ and PR$^+$, or FACT$^+$ and PR$^+$, or ER$^+$ and HER2$^+$ and FACT$^+$, or ER$^+$ and HER2$^+$ and PR$^+$, or ER$^+$ and FACT$^+$ and PR$^+$, or HER2$^+$ and FACT$^+$ and PR$^+$, or ER$^+$ and HER2$^+$ and FACT$^+$ and PR$^+$, or ER$^-$, or HER2$^-$, or FACT$^-$, or PR$^-$, or ER$^-$ and HER2$^-$, or ER$^-$ and FACT$^-$, or ER$^-$ and PR$^-$, or HER2$^-$ and FACT$^-$, or HER2$^-$ and PR$^-$, or FACT$^-$ and PR$^-$, or ER$^-$ and HER2$^-$ and FACT$^-$, or ER$^-$ and HER2$^-$ and PR$^-$, or ER$^-$ and FACT and PR$^-$, or HER2$^-$ and FACT and PR$^-$, or ER$^-$ and HER2$^-$ and FACT and PR$^-$) using methods known in the art and/or described herein. These methods include, but are not limited to, flow cytometry (including, for example, fluorescent activating cell sorting (FACS)), solid phase enzyme-linked immunosorbent assay (ELISA), western blotting (including in cell western), immunofluorescent staining, micro engraving (see, e.g., Lab Chip. 2010; 10(11): 1391-1400), immunofluorescent staining of incorporated bromodeoxyuridine (BrdU) or 7-aminoactinomycin D (7-AAD); ELISPOT assays; mRNA analysis; quantitative RT-PCR; TaqMan Q-PCR; histology; laser capture microdissection; bioluminescent imaging; and assays measuring T cells presented with tumor antigens (Hishii, et al., (1997). Proc. Natl. Acad Sci (USA), 94:1378; Ramirez-Montagut, et al., (2000). 119:11; Kradin, et al., (1989). Lancet, 1:577; Hishii, et al., (1999). Clin Exp Immunol, 116:388; and Pandolfi, et al., (1991). Cancer Res., 51:3164). These methods also include other methods known in the art (see, e.g. Current Protocols in Immunology (2013) by Wiley and Sons).

In various embodiments, the present invention pertains to methods of treating cancer induced by a carcinogen. In some embodiments, the invention pertains to methods of treating cancer induced by a genotoxic carcinogen.

In some embodiments, the carcinogen is one that is classified by the International Agency for Research on Cancer's (IARC) *Monographs on the Evaluation of Carcinogenic Risks to Humans*, including, Group 1 carcinogens (agents that are definitely carcinogenic to humans. The exposure circumstance entails exposures that are carcinogenic to humans), Group 2A (agents that are probably carcinogenic to humans. The exposure circumstance entails exposures that are probably carcinogenic to humans), Group 2B carcinogens (agents that are possibly carcinogenic to humans. The exposure circumstance entails exposures that are possibly carcinogenic to humans), Group 3 carcinogens (agents that are not classifiable as to its carcinogenicity to humans) and Group 4 carcinogens (agents that are probably not carcinogenic to humans). Non-limiting exemplary carcinogens are dioxins and dioxin-like compounds, benzene, kepone, EDB, asbestos, industrial smoke and tobacco smoke, benzo[a]pyrene, nitrosamines (such as nitrosonornicotine), and reactive aldehydes (such as formaldehyde), vinyl chloride, arsenic, asbestos, cadmium, hexavalent chromium(VI) compounds, Diesel exhaust, Ethylene oxide, Nickel, Radon and its decay products, Radium-226, Radium-224, Plutonium-238, Plutonium-239, and other alpha particle emitters with high atomic weight, etc.

In some embodiments, the carcinogen is a dimethylhydrazine (DMH). In particular embodiments, the carcinogen is 1,2-DMH and/or its nonsymmetrical analog 1,1-DMH. In some embodiments, these methods comprise administering an effective amount of a compound described herein. In some embodiments, these methods comprise administering an effective amount of a compound of Formula I or a pharmaceutically acceptable salt thereof. In some embodiments, these methods comprise administering an effective amount of curaxin 137 or a pharmaceutically acceptable salt thereof.

Both 1,2-DMH and its nonsymmetrical analog 1,1-DMH are human carcinogens. Hydrazine and its derivatives are officially declared human carcinogens in the Russian Federation laws (Sanitation Regulation and Hygienic norms 1.2.2353-08 "Carcinogenic factors and main requirements to prevention of carcinogenic risk"). 1,1 DMH is widely used in aerospace industry as an important component of rocket fuel. Thousands of people are engaged in its production and usage, many of them are within a carcinogen high-risk group because they have symptoms of chronic poisoning by 1,1 DMH.

1,2-DMH is considered to be an "absolute carcinogen," i.e. it may not only initiate tumor formation but also to promote its progression. Without wishing to be bound by theory, DMH itself is not believed to directly cause mutations. However, when it is introduced into an organism, it may undergo a metabolic transformation in liver and other tissues which are affected by microsomal oxidation of xenobiotics. Co-products of these reactions include the formation of alkylated derivatives, which have ability to damage DNA. Without intending to be bound by theory, it is believed that formation of active oxygen as a result of metabolic transformations of DMH results in its ability to promote tumor growth. At the level of molecular signal transfer, tumor promotion is modulated by activity of stress pathways components of which include transcription factor p53, NF-kB and phosphatidylinositol-3-kinase/mTOR.

Without wishing to be bound by theory, DMH has a signature for cancer development—the pro-mutagenic lesion O6-MeG, which induces GC to AT transitions in vitro and in vivo. This is the only mutation induced in *E. coli* and *Salmonella* following DMH exposure. Further GC to AT mutations have been detected in the K-ras proto-oncogene in DMH-induced tumors in rats.

DMH induces tumors of many varieties, including, but not limited to adenocarcinomas and polyps of large intestine, squamous cell carcinomas of perianal skin hepatomas and hemangioendotheliomas; tumors, uterine sarcomas, ovarian adenocarcinomas; angiosarcomas of the adrenal glands, and cystic and solid renal adenomas.

In one aspect, the present invention provides a method for treating breast cancer in a subject in need thereof comprising administering an effective amount of a compound of Formula I as defined above or a pharmaceutically acceptable salt or hydrate thereof, wherein the breast cancer is one or more of estrogen receptor positive ($ER^+$), human epidermal growth factor receptor 2 positive ($HER2^+$), progesterone receptor positive (PR+), and facilitates chromatin transcription positive (FACT).

In another aspect, the present invention provides a method for treating breast cancer in a subject in need thereof comprising administering an effective amount of curaxin 137 or a pharmaceutically acceptable salt or hydrate thereof, wherein the breast cancer is one or more of estrogen receptor positive ($ER^+$), human epidermal growth factor receptor 2 positive ($HER2^+$), progesterone receptor positive (PR+), and facilitates chromatin transcription positive (FACT).

In some embodiments the compound of Formula I or a pharmaceutically acceptable salt is administered in combination with an additional cancer therapy, such as, for example, hormone therapy. Such combination therapies are described herein.

In various embodiments, the subject does not receive hormone therapy or hormone therapy was ineffective.

In some embodiments, the cancer is multidrug resistant. For example, the patient may have undergone one or more cycles of chemotherapy, without substantial response. Alternatively or in addition, the tumor has one or more markers of multidrug resistance. Such markers can include chemoresponse assays or molecular assays. Thus the term multidrug resistant includes a cancer that has exhibited non-responsiveness to at least one cycle of combination chemotherapy, or alternatively, has scored (diagnostically) as resistant to at least two of (including comparable agent to) docetaxel, paclitaxel, doxorubicin, epirubicin, carboplatin, cisplatin, vinblastine, vincristine, oxaliplatin, carmustine, fluorouracil, gemcitabine, cyclophosphamide, ifosfamide, topotecan, erlotinib, etoposide, and mitomycin.

In various embodiments, the breast cancer is resistant to platinum drugs and/or taxanes, or is determined to be resistant to platinum drugs or taxanes based on a chemosensitivity test or surrogate biomarker.

As is known in the art, taxanes are a group of drugs that includes, but is not limited to, paclitaxel (TAXOL) and docetaxel (TAXOTERE). Taxanes, without wishing to be bound by theory, prevent the growth of cancer cells by affecting microtubules, which play an important role in cell function. Platinum (Pt) is a naturally occurring element. Platinum drugs, without wishing to be bound by theory, cause cell death by the formation of chemical cross-links in DNA that interfere with DNA replication and transcription. Platinum drugs are a group of drugs that includes, but is not limited to, cisplatin (PLATINOL), carboplatin (PARAPLATIN), and oxaliplatin (ELOXATIN).

In various embodiments, the compound of Formula I or a pharmaceutically acceptable salt is administered as an adjuvant therapy after resection, including, without limitation, as the sole adjuvant therapy.

Adjuvant therapy, also called adjuvant care, is treatment that is given in addition to the primary, main or initial treatment. By way of non-limiting example, adjuvant therapy may be an additional treatment usually given after surgery where all detectable disease has been removed, but where there remains a statistical risk of relapse due to occult disease. In some embodiments, a compound of Formula I or a pharmaceutically acceptable salt thereof is used as an adjuvant therapy in the treatment of breast cancer, including the subtypes described herein. In some embodiments, a compound of Formula I or a pharmaceutically acceptable salt thereof is used as the sole adjuvant therapy in the treatment of breast cancer, including the subtypes described herein.

In some embodiments the compound of Formula I or a pharmaceutically acceptable salt is administered as a neoadjuvant therapy prior to resection.

In certain embodiments, neoadjuvant therapy refers to therapy to shrink and/or downgrade the tumor prior to any surgery. In some embodiments, neoadjuvant therapy means chemotherapy administered to cancer patients prior to surgery. In some embodiments, neoadjuvant therapy means an agent described herein administered to cancer patients prior to surgery. Types of cancers for which neoadjuvant chemotherapy is commonly considered include, for example, breast, colorectal, ovarian, cervical, bladder, and lung. In some embodiments, a compound of Formula I or a pharmaceutically acceptable salt thereof is used as a neoadjuvant therapy in the treatment of breast cancer, including the subtypes described herein. In some embodiments, a compound of Formula I or a pharmaceutically acceptable salt thereof is used as a neoadjuvant therapy in the treatment of breast cancer, including the subtypes described herein, prior to resection.

In some embodiments, resection includes, but is not limited to, a) lumpectomy for breast cancer (breast-conserving therapy)—the cancerous area and a surrounding margin of normal tissue is removed. A second incision may be made in order to remove the lymph nodes. This treatment aims to maintain a normal breast appearance when the surgery is over; b) partial or segmental mastectomy or quadrantectomy—more breast tissue than with a lumpectomy is removed. The cancerous area and a surrounding margin of normal tissue are removed; c) simple or total mastectomy—the entire breast is removed, but no lymph nodes are removed. Simple mastectomy is most frequently used to prevent new cancer from developing or when the cancer does not go to the lymph nodes; and d) modified radical mastectomy—all of the breast tissue along with the nipple is removed. Lymph nodes in the armpit are also sampled. The chest muscles are left intact.

In some embodiments, the invention relates to prevention of cancer. In some embodiments, the present invention provides a method for preventing cancer in a subject comprising administering an effective amount of a compound of Formula I or a pharmaceutically acceptable salt thereof. In some embodiments, the invention provides a method for preventing breast cancer in a subject comprising administering an effective amount of a compound of Formula I or a pharmaceutically acceptable salt thereof. In various embodiments, a compound of Formula I or a pharmaceutically acceptable salt thereof may be administered with an additional therapeutic.

In some embodiments, the preventive methods comprise administering an agent to a subject that is likely to be afflicted by cancer. In some embodiments, a subject is likely to be afflicted by cancer if the subject is characterized by one or more of a high risk for a cancer, a genetic predisposition to a cancer (e.g. genetic risk factors), a previous episode of a cancer (e.g. new cancers and/or recurrence), a family history of a cancer, and exposure to a cancer-inducing agent (e.g. an environmental agent).

In some embodiments, a subject is likely to be afflicted by cancer if the subject is characterized by a high risk for a cancer. In some embodiments, a subject is likely to be afflicted by cancer if the subject is characterized by a genetic predisposition to a cancer. In some embodiments, a genetic predisposition to a cancer is a genetic risk factor, as is known in the art. Such risk factors may include, by way of example, HNPCC, MLH1, MSH2, MSH6, PMS1, PMS2 for at least colon, uterine, small bowel, stomach, urinary tract cancers. In some embodiments, a subject is likely to be afflicted by cancer if the subject is characterized by a previous episode of a cancer. In some embodiments, the subject has been afflicted with 1, or 2, or 3, or 4, or 5, or 6, previous episodes of cancer. In some embodiments, a subject is likely to be afflicted by cancer if the subject is characterized by a family history of a cancer. In some embodiments, a parent and/or grandparent and/or sibling and/or aunt/uncle and/or great aunt/great uncle, and/or cousin has been or is afflicted with a cancer. In some embodiments, a subject is likely to be afflicted by cancer if the subject is characterized by exposure to a cancer-inducing agent (e.g. an environmental agent). For example, exposing skin to strong sunlight is a risk factor for skin cancer. By way of example, smoking is a risk factor for cancers of the lung, mouth, larynx, bladder, kidney, and several other organs.

For example, in the context of breast cancer, any one of the following risk factors may be useful in selecting a subject for cancer prevention with the agents described herein: gender (e.g. breast cancer is more common in females over males); aging (e.g. breast cancer is more prevalent with increased age); genetic risk factors (by way of limiting example, the presence of a mutation in one or more of BRCA1 and BRCA2, ATM (e.g. inheriting a single mutated copy of this gene), TP53 (e.g. subjects afflicted by Li-Fraumeni syndrome), CHEK2 (e.g. subjects afflicted by Li-Fraumeni syndrome), PTEN (e.g. subjects afflicted by Cowden syndrome), CDH1, STK11 (e.g. subjects afflicted by Peutz-Jeghers syndrome); family history of breast cancer (e.g. having one first-degree relative (e.g. mother, sister, or daughter) with breast cancer approximately doubles a woman's risk); personal history of breast cancer; race and ethnicity; features of the breast tissues (e.g. the presence of dense breast tissue, such as those caused by, for example, age, menopausal status, the use of drugs (such as menopausal hormone therapy), pregnancy, and genetics); various benign breast conditions (e.g. non-proliferative lesions (including but not limited to fibrosis and/or simple cysts (e.g. fibrocystic disease or changes), mild hyperplasia, adenosis (e.g. non-sclerosing), ductal ectasia, phyllodes tumor (e.g. benign), one or more papilloma, fat necrosis, periductal fibrosis, squamous and apocrine metaplasia, epithelial-related calcifications, mastitis, other benign tumors (including but not limited to lipoma, hamartoma, hemangioma, neurofibroma, adenomyoepthelioma), proliferative lesions without atypia (e.g. usual ductal hyperplasia, fibroadenoma, sclerosing adenosis, several papillomas (called papillomatosis), and radial scar), proliferative lesions with atypia (e.g. atypical ductal hyperplasia (ADH) and atypical lobular hyperplasia (ALH))); presence of lobular carcinoma in situ (LCIS) increased numbers of menstrual periods, previous chest radiation, carcinogen exposure (e.g. diethylstilbestrol exposure).

In specific embodiments, the present invention provides prevention of a cancer induced by a carcinogen. In some embodiments, the carcinogen is 1,2-DMH and/or its nonsymmetrical analog 1,1-DMH. In some embodiments, the present invention includes selecting a subject that has been or will be exposed to a carcinogen.

In another aspect, the present invention provides a method for identifying a subject who has a breast cancer tumor and is likely to respond to treatment with a compound of Formula I, comprising evaluating the tumor comprising measuring a presence, absence, or level of at least one of ER, PR, HER2, and FACT; wherein the presence of at least one of ER, PR, HER2, and FACT indicates that the subject is likely to respond to treatment with a compound of Formula I and wherein the compound of Formula I is:

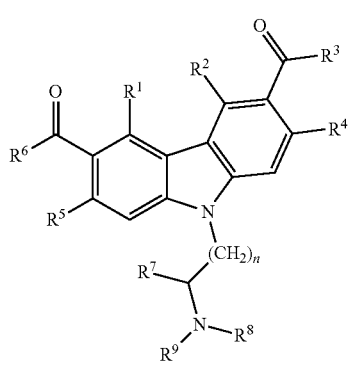

(I)

wherein each of $R^1$—$R^9$ are independently H, hydroxyl or alkyl and n is 0, 1, 2, 3, 4, or 5; or a pharmaceutically acceptable salt or hydrate thereof.

In some embodiments, the method for identifying a subject who has a breast cancer tumor and is likely to respond to treatment with a compound of Formula I further comprises administering an effective amount of the compound of Formula I or a pharmaceutically acceptable salt thereof to a subject that is likely to respond to the compound of Formula I.

In some embodiments, the methods useful for evaluating diagnosis, prognosis, and response to treatment are related to those U.S. Provisional Application No. 61/763,266, filed Feb. 11, 2013, the contents of which are hereby incorporated by reference herein in their entirety Diagnosis refers to the process of attempting to determine or identify a possible disease or disorder, such as, for example, cancer, or breast cancer. Prognosis refers to the predicting of a likely outcome of a disease or disorder, such as, for example, cancer, or breast cancer. A complete prognosis often includes the expected duration, the function, and a description of the course of the disease, such as progressive decline, intermittent crisis, or sudden, unpredictable crisis. Response to treatment is a prediction of a patient's medical outcome when receiving a treatment. Responses to treatment can be, by way of non-limiting example, pathological complete response, survival, and probability of recurrence.

In various aspects, the present invention comprises evaluating a tumor. In various embodiments, the evaluation may be selected from diagnosis, prognosis, and response to treatment.

In various embodiments, the measurement comprises evaluating a presence, absence, or level of a protein. In another embodiment, the measurement comprises evaluating a presence, absence, or level of expression of a nucleic acid.

In still other embodiments, the measurement comprises contacting a specimen of the tumor or cells cultured from the tumor with an agent that specifically binds at least one of ER, PR, HER2, and FACT. In some embodiments, the agent that specifically binds at least one of ER, PR, HER2, and FACT is an antibody.

In still other embodiments, the measurement of at least one of ER, PR, HER2, and FACT comprises one or more of immunohistochemical staining, western blotting, in cell western, immunofluorescent staining, ELISA, and fluorescent activating cell sorting (FACS), or any other method described herein or known in the art.

Methods of an the invention may involve contacting an antibody (e.g. against ER, PR, HER2, and FACT (i.e. FACT and/or SSRP1 and/or SPT16)) with tumor specimen (e.g. biopsy or tissue or body fluid) in order to identify an epitope that is specific to the tissue or body fluid and that is indicative of a state of a cancer (e.g. against ER, PR, HER2, and FACT (i.e. FACT and/or SSRP1 and/or SPT16)).

There are generally two strategies used for detection of epitopes on antigens in body fluids or tissues, direct methods and indirect methods. The direct method comprises a one-step staining, and may involve a labeled antibody (e.g. FITC conjugated antiserum) reacting directly with the antigen in a body fluid or tissue sample. The indirect method comprises an unlabeled primary antibody that reacts with the body fluid or tissue antigen, and a labeled secondary antibody that reacts with the primary antibody. Labels can include radioactive labels, fluorescent labels, hapten labels such as, biotin, or an enzyme such as horse radish peroxidase or alkaline phosphatase. Methods of conducting these assays are well known in the art. See, e.g., Harlow et al. (Antibodies, Cold Spring Harbor Laboratory, NY, 1988), Harlow et al. (Using Antibodies, A Laboratory Manual, Cold Spring Harbor Laboratory, NY, 1999), Virella (Medical Immunology, 6th edition, Informa HealthCare, New York, 2007), and Diamandis et al. (Immunoassays, Academic Press, Inc., New York, 1996). Kits for conducting these assays are commercially available from, for example, Clontech Laboratories, LLC. (Mountain View, Calif.).

In various embodiments, antibodies include whole antibodies and/or any antigen binding fragment (e.g., an antigen-binding portion) and/or single chains of these (e.g. an antibody comprising at least two heavy (H) chains and two light (L) chains inter-connected by disulfide bonds, an Fab fragment, a monovalent fragment consisting of the $V_L$, $V_H$, $C_L$ and CH1 domains; a F(ab)$_2$ fragment, a bivalent fragment including two Fab fragments linked by a disulfide bridge at the hinge region; a Fd fragment consisting of the $V_H$ and CH1 domains; a Fv fragment consisting of the $V_L$ and $V_H$ domains of a single arm of an antibody; and the like). In various embodiments, polyclonal and monoclonal antibodies are useful, as are isolated human or humanized antibodies, or functional fragments thereof.

Standard assays to evaluate the binding ability of the antibodies toward the target of various species are known in the art, including for example, ELISAs, western blots and RIAs. The binding kinetics (e.g., binding affinity) of antibodies also can be assessed by standard assays known in the art, such as by Biacore analysis.

In another embodiment, the measurement comprises evaluating a presence, absence, or level of a nucleic acid.

A person skilled in the art will appreciate that a number of methods can be used to detect or quantify the DNA/RNA levels of ER and/or PR and/or HER2 and/or FACT (i.e. FACT and/or SSRP1 and/or SPT16).

Gene expression can be measured using, for example, low-to-mid-plex techniques, including but not limited to reporter gene assays, Northern blot, fluorescent in situ hybridization (FISH), and reverse transcription PCR (RT-PCR). Gene expression can also be measured using, for example, higher-plex techniques, including but not limited, serial analysis of gene expression (SAGE), DNA microarrays, Tiling array, RNA-Seq/whole transcriptome shotgun sequencing (WTSS), high-throughput sequencing, multiplex PCR, multiplex ligation-dependent probe amplification (MLPA), DNA sequencing by ligation, and Luminex/XMAP.

A person skilled in the art will appreciate that a number of methods can be used to detect or quantify the level of RNA products of the biomarkers within a sample, including arrays, such as microarrays, RT-PCR (including quantitative PCR), nuclease protection assays and Northern blot analyses.

In some embodiments, the present invention includes the measurement of a tumor specimen, including biopsy or surgical specimen samples. In some embodiments, the biopsy is a human biopsy. In various embodiments, the biopsy is any one of a frozen tumor tissue specimen, cultured cells, circulating tumor cells, and a formalin-fixed paraffin-embedded tumor tissue specimen.

In some embodiments, the tumor specimen may be a biopsy sample, such as a frozen tumor tissue (cryosection) specimen. As is known in the art, a cryosection may employ a cryostat, which comprises a microtome inside a freezer. The surgical specimen is placed on a metal tissue disc which is then secured in a chuck and frozen rapidly to about −20° C. to about −30° C. The specimen is embedded in a gel like medium consisting of, for example, poly ethylene glycol and polyvinyl alcohol. The frozen tissue is cut frozen with the microtome portion of the cryostat, and the section is optionally picked up on a glass slide and stained.

In some embodiments, the tumor specimen may be a biopsy sample, such as cultured cells. These cells may be processed using the usual cell culture techniques that are known in the art. These cells may be circulating tumor cells.

In some embodiments, the tumor specimen may be a biopsy sample, such as a formalin-fixed paraffin-embedded (FFPE) tumor tissue specimen. As is known in the art, a biopsy specimen may be placed in a container with formalin (a mixture of water and formaldehyde) or some other fluid to preserve it. The tissue sample may be placed into a mold with hot paraffin wax. The wax cools to form a solid block that protects the tissue. This paraffin wax block with the embedded tissue is placed on a microtome, which cuts very thin slices of the tissue.

In certain embodiments, the tumor specimen contains less than 100 mg of tissue, or in certain embodiments, contains about 50 mg of tissue or less. The tumor specimen (or biopsy) may contain from about 20 mg to about 50 mgs of tissue, such as about 35 mg of tissue.

The tissue may be obtained, for example, as one or more (e.g., 1, 2, 3, 4, or 5) needle biopsies (e.g., using a 14-gauge needle or other suitable size). In some embodiments, the biopsy is a fine-needle aspiration in which a long, thin needle is inserted into a suspicious area and a syringe is used to draw out fluid and cells for analysis. In some embodiments, the biopsy is a core needle biopsy in which a large needle with a cutting tip is used during core needle biopsy to draw a column of tissue out of a suspicious area. In some embodiments, the biopsy is a vacuum-assisted biopsy in which a suction device increases the amount of fluid and cells that is extracted through the needle. In some embodiments, the biopsy is an image-guided biopsy in which a needle biopsy is combined with an imaging procedure, such as, for example, X ray, computerized tomography (CT), magnetic resonance imaging (MRI) or ultrasound. In other embodiments, the sample may be obtained via a device such as the MAMMOTOME® biopsy system, which is a laser guided, vacuum-assisted biopsy system for breast biopsy.

In some embodiments, the present invention provides for the methods for treatment as described herein in which a compound of Formula I or its pharmaceutically acceptable salt may be combined with other anti-cancer treatment modalities. These modalities may include, for example, surgical resection, radiation therapy (including the use of the compounds as described herein as, or in combination with, radiosensitizing agents), chemotherapy, pharmacodynamic therapy, targeted therapy, immunotherapy, and supportive therapy (e.g., painkillers, diuretics, antidiuretics, antivirals, antibiotics, nutritional supplements, anemia therapeutics, blood clotting therapeutics, bone therapeutics, and psychiatric and psychological therapeutics). Such other anti-cancer treatments may be provided sequentially (e.g., before or after) or simultaneously with the administration of a compound of Formula I or its pharmaceutically acceptable salt.

In some embodiments, the present invention provides for the methods for treatment as described herein with a compound of Formula I or its pharmaceutically acceptable salt, and an additional therapeutic, or its pharmaceutically acceptable salt. In some embodiments, the present invention provides for compositions comprising a compound of Formula I or its pharmaceutically acceptable salt, and an additional therapeutic, or its pharmaceutically acceptable salt. In other embodiments, the invention provides for the use of compounds of Formula I or their pharmaceutically acceptable salts, alone or in combination with an additional therapeutic or their pharmaceutically acceptable salts, in the manufacture of a medicament useful for the treatment or prevention of one or more cancers, including breast cancer as described herein.

Such additional therapeutic may be provided sequentially (e.g., before or after) or simultaneously with the administration of a compound of Formula I or its pharmaceutically acceptable salt. In some embodiments, a compound of Formula I or its pharmaceutically acceptable salt may be conjugated to an additional therapeutic.

In embodiments involving conjugation, such conjugates can enhance delivery of the compounds to a particular anatomical site or region of interest (e.g., a tumor), enable sustained therapeutic concentrations of the compounds in target cells, alter pharmacokinetic and pharmacodynamic properties of the compounds, and/or improve the therapeutic index or safety profile of the compounds. Suitable auxiliary moieties include, for example, amino acids, oligopeptides, or polypeptides, e.g., antibodies such as monoclonal antibodies and other engineered antibodies; and natural or synthetic ligands to receptors in target cells or tissues. Other suitable auxiliaries include fatty acid or lipid moieties that promote biodistribution and/or uptake of the compound by target cells (see, e.g., Bradley et al., Clin. Cancer Res. (2001) 7:3229).

In exemplary embodiments, the invention provides various additional therapeutics. Examples of additional therapeutics include, but are not limited to, alkylating agents such as thiotepa and CYTOXAN cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (e.g., bullatacin and bullatacinone); a camptothecin (including the synthetic analogue topotecan); bryostatin; cally statin; CC-1065 (including its adozelesin, carzelesin and bizelesin synthetic analogues); cryptophycins (e.g., cryptophycin 1 and cryptophycin 8); dolastatin; duocarmycin (including the synthetic analogues, KW-2189 and CB 1-TM1);

eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gammaII and calicheamicin omegaII (see, e.g., Agnew, Chem. Intl. Ed. Engl., 33: 183-186 (1994)); dynemicin, including dynemicin A; bisphosphonates, such as clodronate; an esperamicin; as well as neocarzinostatin chromophore and related chromoprotein enediyne antiobiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN doxorubicin (including morpholino-doxorubicin, cyanomorpholino-doxorubicin, 2-pyrrolino-doxorubicin and deoxy doxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as minoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK polysaccharide complex (JHS Natural Products, Eugene, Oreg.); razoxane; rhizoxin; sizofuran; spirogermanium; tenuazonic acid; triaziquone; 2,2',2"-trichlorotriethylamine; trichothecenes (e.g., T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL paclitaxel (Bristol-Myers Squibb Oncology, Princeton, N.J.), ABRAXANE Cremophor-free, albumin-engineered nanoparticle formulation of paclitaxel (American Pharmaceutical Partners, Schaumberg, 111.), and TAXOTERE doxetaxel (Rhone-Poulenc Rorer, Antony, France); chloranbucil; GEMZAR gemcitabine; 6-thioguanine; mercaptopurine; methotrexate; platinum analogs such as cisplatin, oxaliplatin and carboplatin; vinblastine; platinum; etoposide (VP-16); ifosfamide; mitoxantrone; vincristine; NAVELBINE. vinorelbine; novantrone; teniposide; edatrexate; daunomycin; aminopterin; xeloda; ibandronate; irinotecan (Camptosar, CPT-11) (including the treatment regimen of irinotecan with 5-FU and leucovorin); topoisomerase inhibitor RFS 2000; difluoromethylornithine (DMFO); retinoids such as retinoic acid; capecitabine; combretastatin; leucovorin (LV); oxaliplatin, including the oxaliplatin treatment regimen (FOLFOX); lapatinib (Tykerb); inhibitors of PKC-α, Raf, H-Ras, EGFR (e.g., erlotinib (Tarceva)) and VEGF-A that reduce cell proliferation and pharmaceutically acceptable salts, acids or derivatives of any of the above.

Many cancer treatment protocols currently employ radiosensitizers activated by electromagnetic radiation, e.g., X-rays. The present invention also provides for the use of such compounds as additional therapeutics. Examples of X-ray-activated radiosensitizers include, but are not limited to, metronidazole, misonidazole, desmethylmisonidazole, pimonidazole, etanidazole, nimorazole, mitomycin C, RSU 1069, SR 4233, EO9, RB 6145, nicotinamide, 5-bromodeoxyuridine (BUdR), 5-iododeoxyuridine (IUdR), bromodeoxycytidine, fluorodeoxyuridine (FUdR), hydroxyurea, cis-platin, and therapeutically effective analogs and derivatives of the same.

Photodynamic therapy (PDT) employs visible light as the radiation activator of the sensitizing agent. The present invention also provides for the use of such compounds as additional therapeutics. Examples of photodynamic radiosensitizers include, but are not limited to hematoporphyrin derivatives, PHOTOFRIN®, benzoporphyrin derivatives, NPe6, tin etioporphyrin (SnET2), pheoborbide-a, bacteriochlorophyll-a, naphthalocyanines, phthalocyanines, zinc phthalocyanine, and therapeutically effective analogs and derivatives of the same.

In a specific embodiment, the additional therapy is hormone therapy. Hormones and/or steroids (including synthetic analogs) included in the invention include, but are not limited to, 17-α-ethinylestadiol, diethylstilbestrol, testosterone, prednisone, fluoxymesterone, dromostanolone propionate, testolactone, megestrolacetate, methylprednisolone, methyltestosterone, prednisolone, triamcinolone, hlorotrianisene, hydroxyprogesterone, aminogluthimide, estramustine, medroxyprogesteroneacetate, leuprolide, flutarnide, toremifene, zoladex. In some embodiments, the hormone therapy is tamoxifen and toremifene (FARESTON), or fulvestrant (FASLODEX), or megestrol acetate (Megace) or comparable progesterone-like drug or an aromatase inhibitor (e.g. letrozole (FEMARA), anastrozole (ARIMIDEX), and exemestane (AROMASIN), or luteinizing hormone-releasing hormone (LHRH) analogs, such as goserelin (ZOLADEX) or leuprolide (LUPRON), etc.

Any agent described herein can possess a sufficiently basic functional group, which can react with an inorganic or organic acid, or a carboxyl group, which can react with an inorganic or organic base, to form a pharmaceutically acceptable salt. A pharmaceutically acceptable acid addition salt is formed from a pharmaceutically acceptable acid, as is well known in the art. Such salts include the pharmaceutically acceptable salts listed in *Journal of Pharmaceutical Science*, 66, 2-19 (1977) and *The Handbook of Pharmaceutical Salts; Properties*, Selection, and Use. P. H. Stahl and C. G. Wermuth (eds.), Verlag, Zurich (Switzerland) 2002, which are hereby incorporated by reference in their entirety.

Pharmaceutically acceptable salts include, by way of non-limiting example, sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate, camphorsulfonate, pamoate, phenylacetate, trifluoroacetate, acrylate, chlorobenzoate, dinitrobenzoate, hydroxybenzoate, methoxybenzoate, methylbenzoate, o-acetoxybenzoate, naphthalene-2-benzoate, isobutyrate, phenylbutyrate, α-hydroxybutyrate, butyne-1,4-dicarboxylate, hexyne-1,4-dicarboxylate, caprate, caprylate, cinnamate, glycollate, heptanoate, hippurate, malate, hydroxymaleate, malonate, mandelate, mesylate, nicotinate, phthalate, teraphthalate, propiolate, propionate, phenylpropionate, sebacate, suberate, p-bromobenzenesulfonate, chlorobenzenesulfonate, ethylsulfonate, 2-hydroxyethylsulfonate, methylsulfonate, naphthalene-1-sulfonate, naphthalene-2-sulfonate, naphthalene-1,5-sulfonate, xylenesulfonate, and tartarate salts.

The term pharmaceutically acceptable salt also refers to a salt of the compounds of the present invention having an acidic functional group, such as a carboxylic acid functional group, and a base. Suitable bases include, but are not limited to, hydroxides of alkali metals such as sodium, potassium, and lithium; hydroxides of alkaline earth metal such as calcium and magnesium; hydroxides of other metals, such as aluminum and zinc; ammonia, and organic amines, such as unsubstituted or hydroxy-substituted mono-, di-, or tri-alkylamines, dicyclohexylamine; tributyl amine; pyridine; N-methyl, N-ethylamine; diethylamine; triethylamine; mono-, bis-, or tris-(2-OH-lower alkylamines), such as mono-; bis-, or tris-(2-hydroxyethyl)amine, 2-hydroxy-tert-butylamine, or tris-(hydroxymethyl)methylamine, N,N-di-lower alkyl-N-(hydroxyl-lower alkyl)-amines, such as N,N-dimethyl-N-(2-hydroxyethyl)amine or tri-(2-hydroxyethyl)amine; N-methyl-D-glucamine; and amino acids such as arginine, lysine, and the like.

In some embodiments, a representative pharmaceutically acceptable salt includes, e.g., water-soluble and water-insoluble salts, such as the acetate, amsonate (4,4-diaminostilbene-2,2-disulfonate), benzenesulfonate, benzonate, bicarbonate, bisulfate, bitartrate, borate, bromide, butyrate, calcium, calcium edetate, camsylate, carbonate, chloride, citrate, clavulariate, dihydrochloride, edetate, edisylate, estolate, esylate, fumarate, gluceptate, gluconate, glutamate, glycollylarsanilate, hexafluorophosphate, hexylresorcinate, hydrabamine, hydrobromide, hydrochloride, hydroxynaphthoate, iodide, isothionate, lactate, lactobionate, laurate, magnesium, malate, maleate, mandelate, mesylate, methylbromide, methylnitrate, methylsulfate, mucate, napsylate, nitrate, N-methylglucamine ammonium salt, 3-hydroxy-2-naphthoate, oleate, oxalate, palmitate, pamoate (1,1-methene-bis-2-hydroxy-3-naphthoate, einbonate), pantothenate, phosphate/diphosphate, picrate, polygalacturonate, propionate, p-toluenesulfonate, salicylate, stearate, subacetate, succinate, sulfate, sulfosalicylate, suramate, tannate, tartrate, teoclate, tosylate, triethiodide and valerate salts.

Further, any agent described herein can be administered to a subject as a component of a composition that comprises a pharmaceutically acceptable carrier or vehicle. Such compositions can optionally comprise a suitable amount of a pharmaceutically acceptable excipient so as to provide the form for proper administration.

Pharmaceutical excipients can be liquids, such as water and oils, including those of petroleum, animal, vegetable, or synthetic origin, such as peanut oil, soybean oil, mineral oil, sesame oil and the like. The pharmaceutical excipients can be saline, gum acacia, gelatin, starch paste, talc, keratin, colloidal silica, urea and the like. In addition, auxiliary, stabilizing, thickening, lubricating, and coloring agents can be used. In one embodiment, the pharmaceutically acceptable excipients are sterile when administered to a subject. Water is a useful excipient when any agent described herein is administered intravenously. Saline solutions and aqueous dextrose and glycerol solutions can also be employed as liquid excipients, specifically for injectable solutions. Suitable pharmaceutical excipients also include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. Any agent described herein, if desired, can also comprise minor amounts of wetting or emulsifying agents, or pH buffering agents.

Any agent described herein can take the form of solutions, suspensions, emulsion, tablets, pills, pellets, capsules, capsules containing liquids, powders, sustained-release formulations, suppositories, emulsions, aerosols, sprays, suspensions, or any other form suitable for use. Other examples of suitable pharmaceutical excipients are described in Remington's Pharmaceutical Sciences 1447-1676 (Alfonso R. Gennaro eds., 19th ed. 1995), incorporated herein by reference.

In one embodiment, any agent described herein is formulated in accordance with routine procedures as a composition adapted for oral administration to human beings. Compositions for oral delivery can be in the form of tablets, lozenges, aqueous or oily suspensions, granules, powders, emulsions, capsules, syrups, or elixirs, for example. Orally administered compositions can comprise one or more agents, for example, sweetening agents such as fructose, aspartame or saccharin; flavoring agents such as peppermint, oil of wintergreen, or cherry; coloring agents; and preserving agents, to provide a pharmaceutically palatable preparation. Moreover, where in tablet or pill form, the compositions can be coated to delay disintegration and absorption in the gastrointestinal tract thereby providing a sustained action over an extended period of time. Selectively permeable membranes surrounding an osmotically active driving any agent described herein are also suitable for orally administered compositions. In these latter platforms, fluid from the environment surrounding the capsule is imbibed by the driving compound, which swells to displace the agent or agent composition through an aperture. These delivery platforms can provide an essentially zero order delivery profile as opposed to the spiked profiles of immediate release formulations. A time-delay material such as glycerol monostearate or glycerol stearate can also be useful. Oral compositions can include standard excipients such as mannitol, lactose, starch, magnesium stearate, sodium saccharin, cellulose, and magnesium carbonate. In one embodiment, the excipients are of pharmaceutical grade.

The ingredients may be supplied either separately or mixed together in unit dosage form, for example, as a pre-mixed solution, dry lyophilized-powder, or water-free concentrate in a hermetically sealed container such as an ampule, pre-filled syringe, or sachette indicating the quantity of active agent. Where any agent described herein is to be administered by infusion, it can be dispensed, for example, with an infusion bottle containing sterile pharmaceutical grade water or saline. Where any agent described herein is to be administered by injection, an ampule of sterile water for injection or saline can be provided so that the ingredients can be mixed prior to administration.

Any agent described herein can be administered by controlled-release or sustained-release means or by delivery devices that are well known to those of ordinary skill in the art. Examples include, but are not limited to, those described in U.S. Pat. Nos. 3,845,770; 3,916,899; 3,536,809; 3,598,123; 4,008,719; 5,674,533; 5,059,595; 5,591,767; 5,120,548; 5,073,543; 5,639,476; 5,354,556; and 5,733,556, each of which is incorporated herein by reference in its entirety. Such dosage forms can be useful for providing controlled- or sustained-release of one or more active ingredients using, for example, hydropropylmethyl cellulose, other polymer matrices, gels, permeable membranes, osmotic systems, multilayer coatings, microparticles, liposomes, microspheres, or a combination thereof to provide the desired release profile in varying proportions. Suitable controlled- or sustained-release formulations known to those skilled in the art, including those described herein, can be readily selected for use with the active ingredients of the agents described herein. The invention thus provides single unit dosage forms suitable for oral administration such as, but not limited to, tablets, capsules, gelcaps, and caplets that are adapted for controlled- or sustained-release.

Controlled- or sustained-release of an active ingredient can be stimulated by various conditions, including but not limited to, changes in pH, changes in temperature, stimulation by an appropriate wavelength of light, concentration or availability of enzymes, concentration or availability of water, or other physiological conditions or compounds.

Compositions can be prepared according to conventional mixing, granulating, coating or polymerization methods, respectively, and the present compositions can comprise, in one embodiment, from about 0.1% to about 99%; and in another embodiment from about 1% to about 70% of any agent described herein by weight or volume.

In another embodiment, any agent described herein acts synergistically when co-administered with another agent and is administered at doses that are lower than the doses commonly employed when such agents are used as monotherapy. For example, in some embodiments, a compound of Formula I or its pharmaceutically acceptable salt and an additional therapeutic, or its pharmaceutically acceptable salt can have greater than additive effects when administered in combination or conjugation. In some embodiments, a compound of Formula I or its pharmaceutically acceptable salt and an additional therapeutic, or its pharmaceutically acceptable salt can have synergistic effects when administered in combination or conjugation.

For example, the dosage any agent described herein as well as the dosing schedule can depend on various parameters, including, but not limited to, the cancer (e.g. breast cancer) being treated, the subject's general health, and the administering physician's discretion. Any agent described herein, can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concurrently with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of an additional therapeutic agent, to a subject in need thereof. In various embodiments any agent described herein is administered 1 minute apart, 10 minutes apart, 30 minutes apart, less than 1 hour apart, 1 hour apart, 1 hour to 2 hours apart, 2 hours to 3 hours apart, 3 hours to 4 hours apart, 4 hours to 5 hours apart, 5 hours to 6 hours apart, 6 hours to 7 hours apart, 7 hours to 8 hours apart, 8 hours to 9 hours apart, 9 hours to 10 hours apart, 10 hours to 11 hours apart, 11 hours to 12 hours apart, no more than 24 hours apart or no more than 48 hours apart.

The amount of any agent described herein that is admixed with the carrier materials to produce a single dosage can vary depending upon the subject being treated and the particular mode of administration. In vitro or in vivo assays can be employed to help identify optimal dosage ranges.

In general, the doses that are useful are known to those in the art. For example, doses may be determined with reference Physicians' Desk Reference, 66th Edition, PDR Network; 2012 Edition (Dec. 27, 2011), the contents of which are incorporated by reference in its entirety.

The dosage of any agent described herein can depend on several factors including the severity of the condition, whether the condition is to be treated or prevented, and the age, weight, and health of the subject to be treated. Additionally, pharmacogenomic (the effect of genotype on the pharmacokinetic, pharmacodynamic or efficacy profile of a therapeutic) information about a particular subject may affect dosage used. Furthermore, the exact individual dosages can be adjusted somewhat depending on a variety of factors, including the specific combination of the agents being administered, the time of administration, the route of administration, the nature of the formulation, the rate of excretion, the particular cancer (e.g. type of breast cancer) being treated, the severity of the disorder, and the anatomical location of the disorder. Some variations in the dosage can be expected.

Generally, when orally administered to a mammal, the dosage of any agent described herein may be 0.001 mg/kg/day to 100 mg/kg/day, 0.01 mg/kg/day to 50 mg/kg/day, or 0.1 mg/kg/day to 10 mg/kg/day. When orally administered to a human, the dosage of any agent described herein is normally 0.001 mg to 1000 mg per day, 1 mg to 600 mg per day, or 5 mg to 30 mg per day. In one embodiment, oral dosage is 600 mg per day. In one embodiment, the oral dosage is two 300 mg doses per day. In another embodiment, oral dosage is 7.5 mg per week to 15 mg per week.

For administration of any agent described herein by parenteral injection, the dosage is normally 0.1 mg to 250 mg per day, 1 mg to 20 mg per day, or 3 mg to 5 mg per day. Injections may be given up to four times daily. Generally, when orally or parenterally administered, the dosage of any agent described herein is normally 0.1 mg to 1500 mg per day, or 0.5 mg to 10 mg per day, or 0.5 mg to 5 mg per day. A dosage of up to 3000 mg per day can be administered.

In some embodiments, non-limiting examples of the dose of a compound of Formula I or its pharmaceutically acceptable salt and an additional therapeutic or its pharmaceutically acceptable salt (in combination or administered individually) may be in a range of about 0.1 mg/kg to about 100 mg/kg of body weight of the subject, for example, about 0.1 mg/kg, about 0.2 mg/kg, about 0.3 mg/kg, about 0.4 mg/kg, about 0.5 mg/kg, about 0.6 mg/kg, about 0.7 mg/kg, about 0.8 mg/kg, about 0.9 mg/kg, about 1 mg/kg, about 1.1 mg/kg, about 1.2 mg/kg, about 1.3 mg/kg, about 1.4 mg/kg, about 1.5 mg/kg, about 1.6 mg/kg, about 1.7 mg/kg, about 1.8 mg/kg, about 1.9 mg/kg, about 2 mg/kg, about 3 mg/kg, about 4 mg/kg, about 5 mg/kg, about 6 mg/kg, about 7 mg/kg, about 8 mg/kg, about 9 mg/kg, about 10 mg/kg, about 11 mg/kg, about 12 mg/kg, about 13 mg/kg, about 14 mg/kg, about 15 mg/kg, about 20 mg/kg, about 25 mg/kg, about 30 mg/kg, about 35 mg/kg, about 40 mg/kg, about 45 mg/kg, about 50 mg/kg, about 55 mg/kg, about 60 mg/kg, about 65 mg/kg, about 70 mg/kg, about 75 mg/kg, about 80 mg/kg, about 85 mg/kg, about 90 mg/kg, about 95 mg/kg, or about 100 mg/kg body weight, inclusive of all values and ranges therebetween.

Routes of administration may include, for example: intradermal, intramuscular, intraperitoneal, intravenous, subcutaneous, intranasal, epidural, oral, sublingual, intranasal, intracerebral, intravaginal, transdermal, rectally, by inhalation, or topically, particularly to the ears, nose, eyes, or skin.

The mode of administration can be left to the discretion of the practitioner, and depends in-part upon the site of the medical condition. In most instances, administration results in the release of any agent described herein into the bloodstream.

Any agent described herein can be administered orally. Such agents can also be administered by any other convenient route, for example, by intravenous infusion or bolus injection, by absorption through epithelial or mucocutaneous linings (e.g., oral mucosa, rectal and intestinal mucosa, etc.) and can be administered together with another biologically active agent. Administration can be systemic or local. Various delivery systems are known, e.g., encapsulation in liposomes, microparticles, microcapsules, capsules, etc., and can be used to administer.

In specific embodiments, it may be desirable to administer locally to the area in need of treatment.

In another embodiment, delivery can be in a vesicle, in particular a liposome (see Langer, 1990, Science 249:1527-1533; Treat et al., in *Liposomes in the Therapy of Infectious Disease and Cancer*, Lopez-Berestein and Fidler (eds.), Liss, New York, pp. 353-365 (1989). In yet another embodiment, delivery can be in a controlled release system. In one embodiment, a slow release device may be used. In some embodiments, this device consists of a locally delivered erodible or non-erodible liquid, gel, polymer, etc.

In another embodiment, polymeric materials can be used (see *Medical Applications of Controlled Release*, Langer and Wise (eds.), CRC Pres., Boca Raton, Fla. (1974); *Controlled Drug Bioavailability, Drug Product Design and Performance*, Smolen and Ball (eds.), Wiley, New York (1984); Ranger and Peppas, 1983, *J. Macromol. Sci. Rev. Macromol. Chem.* 23:61; see also Levy et al., 1985, *Science* 228:190; During et al., 1989, *Ann. Neurol.* 25:351; Howard et al., 1989, *J. Neurosurg.* 71:105). In another embodiment, a controlled-release system can be placed in proximity of the target area to be treated, thus requiring only a fraction of the systemic dose (see, e.g., Goodson, in *Medical Applications of Controlled Release*, supra, vol. 2, pp. 115-138 (1984)). Other controlled-release systems discussed in the review by Langer, 1990, *Science* 249:1527-1533) may be used.

Administration of any agent described herein can, independently, be one to four times daily or one to four times per month or one to six times per year or once every two, three, four or five years. Administration can be for the duration of one day or one month, two months, three months, six months, one year, two years, three years, and may even be for the life of the subject. Chronic, long-term administration may be indicated in some cases. The dosage may be administered as a single dose or divided into multiple doses. In general, the desired dosage should be administered at set intervals for a prolonged period, usually at least over several weeks or months, although longer periods of administration of several months or years or more may be needed.

The dosage regimen utilizing any agent described herein can be selected in accordance with a variety of factors including type, species, age, weight, sex and medical condition of the subject; the severity of the condition to be treated; the route of administration; the renal or hepatic function of the subject; the pharmacogenomic makeup of the individual; and the specific compound of the invention employed. Any agent described herein can be administered in a single daily dose, or the total daily dosage can be administered in divided doses of two, three or four times daily. Furthermore, any agent described herein can be administered continuously rather than intermittently throughout the dosage regimen.

The dosage administered is an effective amount of the agent. Effective amounts, toxicity, and therapeutic efficacy can be determined by standard pharmaceutical procedures in cell cultures or experimental animals, including but not limited to, determining the $LD_{50}$ (the dose lethal to about 50% of the population) and/or the $ED_{50}$ (the dose therapeutically effective in about 50% of the population). The dosage can vary depending upon the dosage form employed and the route of administration utilized. The dose ratio between toxic and therapeutic effects is the therapeutic index and can be expressed as the ratio $LD_{50}/ED_{50}$. Compositions and methods that exhibit large therapeutic indices may be selected for use, in some embodiments.

A therapeutically effective dose can be estimated initially from cell culture assays. Also, a dose can be formulated in animal models to achieve a circulating plasma concentration range that includes the $IC_{50}$ (e.g., the concentration of a compound of Formula I and/or additional therapeutic or a pharmaceutically acceptable salt thereof), which achieves a half-maximal inhibition of symptoms) as determined in cell culture, or in an appropriate animal model. Levels in plasma can be measured, for example, by high performance liquid chromatography. The effects of any particular dosage can be monitored by a suitable bioassay. The dosage can be determined by a physician and adjusted, as necessary, to suit observed effects of the treatment.

For example, the potency a compound of Formula I or a pharmaceutically acceptable salt thereof may be evaluated by measuring an ability of the compound to inhibit NF-κB activity or to activate p53. Activation of p53 may be measured using a dose-response assay in which a sensitive assay system is contacted with a compound of interest over a range of concentrations, including concentrations at which no or minimal effect is observed, through higher concentrations at which partial effect is observed, to saturating concentrations at which a maximum effect is observed. Theoretically, such assays of the dose-response effect of activator compounds can be described as a sigmoidal curve expressing a degree of activation as a function of concentration. The curve also theoretically passes through a point at which the concentration is sufficient to increase activity to a level that is 50% that of the difference between a baseline and the maximal activity in the assay—the $EC_{50}$ value. Determination of an EC50 value is made using conventional biochemical (acellular) assay techniques or cell-based assay techniques.

Comparisons of the efficacy of activators often are provided with reference to comparative $EC_{50}$ values, wherein a higher $EC_{50}$ indicates that the test compound is less potent, and a lower EC50 indicates that the compound is more potent, than a reference compound. Compounds of the present invention exhibit unexpectedly good potency, e.g., p53 activation, in a luciferase reporter cell line assay.

In some embodiments, the effect will result in a quantifiable change of at least about 10%, preferably at least about 20%, about 30%, about 50%, about 70%, or about 90% or more. Therapeutic benefit also includes halting or slowing the progression of the underlying disease or disorder, regardless of whether improvement is realized.

In certain embodiments, an effective amount that will treat cancer will modulate the symptoms typically by at least about 10%, at least about 20%, at least about 30%, at least about 40%, or at least about 50%. In exemplary embodiments, such modulations will result in, for example, statistically significant and quantifiable changes in the numbers of cancerous cells. In some embodiments, this may be a decrease in the numbers of micrometastases in distant organs, a decrease in recurrent metastatic disease, etc.

This invention is further illustrated by the following non-limiting examples.

EXAMPLES

Example 1

Curaxin-137 Has Anti-Tumor Efficacy When Administered To Tumor-Prone MMTV-Neu Female Mice The methods employed herein are known in the art. Details of some of these methods are provided below.

Chemical and Reagents: curaxin-137 also known as CBLC137 (>97% pure by HPLC and LC/MS) was custom synthesized by Dalton Pharma (Toronto, Canada). For administration to animals, the drug was dissolved in water at 0.1 or 0.2 mg/ml and stored at room temperature (RT). The stability of the compound in water at RT was tested over 2 months in a standard p53 activation reporter assay on RCC45-p53-Luc cells as described (see Sci Transl Med 2011 Aug. 10; 3(95):95ra74). No difference between fresh and stored solutions was found. Hoechst 33358, R1881, TNF, type III collagenase, hydrocortisone, insulin and EGF were purchased from Sigma (Sigma-Aldrich, Inc). 100× penicillin/streptomycin and fungizone solutions, DMEM, glutamine, N-(2-hydroxyethyl)piperazine-N'-ethanesulfonic acid (HEPES), bovine serum albumin (BSA), cholera toxin and Trizol were purchased from Invitrogen, Inc.

Cells: MDA-MB-453-MMTV-luc (KB2) cells were purchased from ATCC. H1299-KB-Luc and RCC45-p53-Luc cells were described previously (see Proc Natl Acad Sci USA 2005 Nov. 29; 102(48):17448-53). Cells were grown in DMEM with 10% fetal bovine serum (Hyclone) and other standard supplements.

Ex vivo cell culture: tumor free mammary glands or necrosis-free mammary tumors were isolated from deeply anesthetized mice under sterile conditions, washed in PBS, minced with scissors and then incubated in 0.1% Type III Collagenase in complete culture medium (DMEM supplemented with 100 U/ml penicillin, 100 pg/ml streptomycin, 2 mM glutamine, 10 mM HEPES, 0.075% BSA, 10 ng/ml cholera toxin, 0.5 pg/ml hydrocortisone, 5 pg/ml insulin, and 5 ng/ml EGF) overnight at 37° C. on a shaking platform. After incubation, the cell suspension was centrifuged at 40 g for 1 min. The supernatant was discarded and the pellet was washed once with PBS using the same centrifugation conditions. The final pellet was resuspended in complete culture medium and plated into plastic plates. The resulting "organoid" culture was used for an experiment within one week without additional replating.

Western blotting and immunofluorescent staining were performed using standard procedures. The following primary antibodies were used: anti-ERα (SC-542, Santa Cruz, dilution for WB was 1:1000, IF 1:100), anti-Her2 (cat#2165, Cell Signaling, dilution for WB was 1:1000, IF 1:200), anti-PCNA (cat#2586, Cell Signaling, dilution for WB was 1:1000, IF 1:300), anti-SSRP1 cat#60970, Biolegend, dilution for WB was 1:1000, IF 1:200), anti-SPT16 (cat#607002, Biolegend, dilution for WB was 1:1000, IF 1:200), anti-p53 (Pab421, SC-99 Santa Cruz, dilution for WB was 1:1000, IF 1:200), anti-p65 (SC372 Santa Cruz, dilution for IF was 1:200), anti-β-actin (A3854, Sigma, dilution for WB was 1:20,000) secondary anti-mouse or anti-rabbit antibodies conjugated with either horse radish peroxidase (Cell Signaling, dilution for WB was 1:2) or Alexa Fluor 488 or 594 (A21202, A21207, Invitrogen, dilution for IF was 1:500).

Immunohistochemistry: Paraffin sections were cut at 5 µm, placed on charged slides, and dried at 60° C. for one hour. Slides were cooled to RT, deparaffinized in three changes of xylene, and rehydrated using graded alcohols. Endogenous peroxidase was quenched with aqueous 3% $H_2O_2$ For antigen retrieval, slides were heated in a microwave for 20 m in citrate buffer (pH 6.0), cooled for 15 min and washed in 0.1% PBS/Tween20 solution. Slides were then loaded onto a Dako Autostainer and blocked for 5 minutes with serum-free protein block (Dako). After blocking, the slides were incubated with 0.2 µg/ml goat anti-mouse SSRP1 polyclonal antibody (Santa Cruz, sc-5909) for 1 hour. An isotype-matched control antibody (0.2 µg/ml goat IgG) was used on a duplicate slide in place of the primary antibody as a negative control. After washing, slides were incubated with biotinylated donkey anti-goat IgG (Jackson ImmunoResearch Laboratories, Inc.), followed by staining with the Elite ABC Kit (Vectastain), and DAB chromagen (Dako). Finally, stained slides were counterstained with Hematoxylin, dehydrated, cleared and cover-slipped. All slides were scanned using Aperio scanscope (Aperio Technologies, Inc). Images were made using Image scope software (Aperio Technologies, Inc).

Microarray-based gene expression profiling: total RNA was isolated from frozen tissue samples using TRIZOL reagent (Invitrogen). mRNA labeling and hybridization to MouseWG-6 v2.0 Expression. BeadChips, image scanning, and intensity processing were performed according to the manufacturer's instructions (Illumina, San Diego, Calif.). BeadChip data files were analyzed with Illumina's GenomeStudio software and R-based Bioconductor package to determine gene expression signal levels. A hierarchical clustering algorithm based on the average linkage of Pearson correlations was employed. Data are deposited at NCBI GEO database, accession number GSE33285.

Measurement of curaxin-137 concentrations in mouse tissues and plasma: drug compound extraction was done in the Department of Chemistry at Cleveland BioLabs. From an original tissue specimen, a 70-100 mg sample was weighed out. Chilled Methanol (9× sample weight) was added to the sample and the sample was mechanically homogenized (Fisher Scientific PowerGen 125). The resulting sample/methanol suspension was then rocked overnight in a 4° C. refrigerator. The samples were then centrifuged and the supernatant was taken for analysis by LC/MS/MS. The plasma samples were extracted using an extraction solution of 0.1% Trifluoroacetic acid in Acetonitrile (4× sample volume). The diluted samples were vortexed thoroughly then centrifuged and the resulting supernatant was taken for analysis by LC/MS/MS. All prepared samples were stored at 4° C. until analyzed. The samples were analyzed for curaxin-137 using an Applied Biosystems API 3000 LC/MS/MS system. A gradient HPLC method was employed with mobile phases: (A) 2 mM Ammonium acetate, 0.1% Trifluoroacetic acid in Water and (B) 2 mM Ammonium acetate, 0.1% Trifluoroacetic acid in Methanol. The injection volume was 20 µL and the flow rate 0.20 mL/min. A Phenomenex Luna column C18(2), 50×2.00 mm, 5 µm particle size was coupled with a Phenomenex C18, 4×2.00 mm guard cartridge/column. The mass spectrometer used multiple reaction monitoring (MRM) with the singly charged curaxin-137 selected at m/z 337.20 giving a fragment ion at m/z 86.00.

Animal Experiments: all animal experiments were performed according to the Roswell Park Cancer Institute ("RPCI") IACUC-approved protocol and with guidance from the "Guide for the Care and Use of Laboratory Animals" by the National Research Council (ISBN 0-309-05377-3). FVB/N-Tg(MMTVneu)202Mul/J mice (referred to herein as "MMTV-neu mice") were obtained from The Jackson Laboratory (Bar Harbor, Me.) and bred as necessary in the department of Laboratory Resources (LAR) of RPCI. The transgene carried by these mice directs expression of the Her2/neu proto-oncogene from the steroid receptor, in females mostly estrogen receptor (ER)-responsive MMTV promoter. 100% of female MMTV-neu mice develop spontaneous mammary carcinomas between 6 and 12 months of age.

Detection of the maximal tolerated dose (MTD) of Curaxin-137 administered to mice in their drinking water: groups of 5 MMTV-neu mice (males and females, 4 weeks old) were placed in a cage and provided with a solution of curaxin-137 (various concentrations as described below) in water in dark bottles (at least 150 ml per bottle) as the only source of water. Bottles were weighed before the start of the experiment and once a week thereafter. Bottles were refilled once a week. Mice were given a standard diet ad libitum. Mice were observed daily for changes in appearance and behavior and were weighed daily during the first week and then once weekly. The experiment was run for one month or until any of the following conditions were observed: ≥10% loss of weight (all 5 mice in a group); ≥15% loss of weight by 2 and more animals in a group; consistent changes in mouse visual appearance or behavior; death of more than one animal in a cage. Starting doses tested in this experiment were calculated based on average mouse daily liquid consumption of 150 ml/kg/day taken from several reference sources and then adjusted based in actual liquid consumption in LAR facility of RPCI.

Safety of chronic administration of Curaxin-137 at MTD and ½ MTD in drinking water: groups of 5 male MMTV-neu mice (4 weeks of age) were given either plain water or solutions of curaxin-137 (at MTD or ½ MTD) in water ad libitum for 10 weeks. Mice were weighed once a week. After 10 weeks. mice were deeply anesthetized and blood was collected by cardiac puncture for plasma isolation. Major organs were collected for histopathological analysis, RNA isolation and measurement of curaxin-137 concentration.

Cancer prevention study: virgin female MMTV-neu mice (19-27 per group) were given either plain water or curaxin-137 in water ad libitum. Curaxin-treated groups were given either 0.1 mg/ml curaxin-137 starting at 4 weeks of age or 0.2 mg/ml curaxin-137 starting at 10 weeks of age). Animals were monitored daily for signs of abnormalities and tumor appearance. They were weighed once a week for the first 24 weeks and then once a month. Animals that developed at least one visible tumor were transferred to drug-free water and kept until their cumulative tumor volume reached 2000 mm$^3$. At that time, mice were sacrificed and all mammary glands with and without tumors were excised, fixed in buffered formalin and paraffin embedded for sectioning. Histopathology examination was done blindly by qualified pathologists at an external facility. In addition, H&E-stained slides of mouse parenchymal organs, bone marrow and tumors were analyzed by a qualified animal pathologist in house (I.T.) and representative photographs were taken using a Zeiss Axio Observer A1 inverted microscope with N-achroplan 100x/1.25 oil lens, Zeiss MRCS camera and AxioVision Re1.4.8 software.

Without wishing to be bound by theory, the anti-cancer effects of curaxins on the p53, NF-κB and HSF1 pathways in tumor cells may be due to suppression of activity of the FACT complex.

The role of FACT in tumor transformation was investigated, as was the activity of curaxins in the suppression tumor formation by modulating FACT activity (without wishing to be bound by theory), in precancerous cells. These experiments employed a MMTV-neu transgenic mouse model of mammary carcinogenesis, in which mammary tumor formation is induced through ectopic expression of the Her2/neu proto-oncogene driven by the steroid receptor-responsive promoter from the long terminal repeats of Mouse Mammary Tumor Virus (MMTV) (see, e.g. Cancer Lett 1992 Jul. 10; 64(3):203-9). Transgene expression in these mice is limited to tissues that express steroid receptors and mostly estrogen receptor in female, such as mammary epithelial cells and ovary. Mammary tumors in these animals recapitulate histopathological features of human breast adenocarcinomas (See Breast Cancer Res Treat 1998 January; 47(2):171-80).

A role for p53 suppression and NF-κB activation in promoting tumor formation in the MMTV-neu model was previously demonstrated (see Breast Cancer Res 2007; 9(4):211). Inflammation, which is associated with increased NF-kB activity, is a marker of more aggressive breast cancer and a promoter of tumor formation in the MMTV-neu mouse model (see Breast Cancer Res 2007; 9(4):211). A gradual elevation of FACT subunit expression beginning at the very early stages of transformation in these mice was observed. The curaxin compound, curaxin-137 (a.k.a. CBLC137), had effects on FACT, p53 and NF-κB. These effects were translated into anti-cancer efficacy in MMTV-neu mice treated chronically with curaxin-137 provided with drinking water: tumor onset and progression were suppressed, and the lifespan of MMTV-neu animals treated with curaxin-137 was significantly prolonged as compared to control animals.

The following experiments show, inter alia, that curaxin-137 did not directly interfere with ectopic Her2/neu expression in MMTV-neu mice. In MMTV-neu transgenic mice, mammary tumorigenesis in females is driven by Her2/neu proto-oncogene expression from the estrogen receptor (ER)-regulated MMTV promoter. To test the potential anti-tumor effect of curaxin-137 in this model, it was tested whether the compound has any direct effect on the activity of the MMTV promoter that would alter ectopic expression of Her2/neu. Therefore, the effect of curaxin-137 on a luciferase reporter gene expression from the MMTV promoter in a human breast cancer cell line (MDA-KB2) was evaluated. As a positive control, cells carrying an NF-κB-dependent luciferase reporter, expression of which is known to be inhibited by curaxin-137, was used. Transcriptional activity of steroid receptor (androgen receptor in MDA-KB2 cells) and NF-κB were induced in cells with their corresponding ligands, synthetic androgen, R1881, or TNF respectively, in the presence or absence of different concentrations of curaxin-137 (FIG. 1A and FIG. 1B). Curaxin-137 clearly inhibited NF-κB-dependent reporter activity as early as 3 hours post-treatment, but had no effect on luciferase expression from the MMTV promoter at 3 hours or 6 hours post-treatment, even with high curaxin-137 doses. Inhibition of MMTV-Luc expression was only seen following treatment with high drug concentrations for 24 hours, at which time signs of cell death were apparent.

The effect of curaxin-137 on expression of ER and Her2 in cells of normal mammary glands and mammary tumors from MMTV-neu mice was also tested. Short term ex vivo cultures of disaggregated mammary tumors or normal mammary glands were treated with curaxin-137 for 24 h. Immunofluorescent staining showed that ER expression in normal mammary epithelial cells increased in response to curaxin-137, but no Her2 staining was detected in non-malignant cells (FIG. 1C, upper panel). In contrast, in mammary tumors, expression of ER, Her2, and proliferation, assessed using anti-PCNA antibodies, were all reduced after curaxin-137 treatment (FIG. 1C, lower panel). These expression differences were confirmed by Western blot analysis of protein extracts from normal mammary epithelial cells (FIG. 1D) and mammary tumor cells (FIG. 1E) treated with curaxin-137 ex vivo. These data indicate, without wishing to be bound by theory, that curaxin-137 has different effects on expression of ER and Her2 in normal and tumor cells of mammary glands of MMTV-neu mice, causing a slight dose-dependent bell-shaped increase in the level of ER and Her2 in normal cells, yet reduction of both proteins in tumor cells (FIG. 1D and FIG. 1E). While the mechanism(s) underlying these effects were not investigated further, without wishing to be bound by theory, the observed reduction of ER and Her2 protein levels in curaxin-137-treated tumor cells might be due to curaxin-137-mediated inhibition of heat shock factor 1 (HSF1) transcriptional activity. This may lead to reduced HSF1-dependent expression of chaperones that are known to be critical regulators of ER and Her2 protein stability.

The results described above also show that curaxin-137 does not have any direct inhibiting effect on MMTV promoter activity in mammary cells in this model and, therefore, this model is appropriate for testing the anti-cancer efficacy of curaxin-137.

Next, it was examined whether additional factors, i.e. FACT, p53 and NF-κB, are involved in mammary carcinogenesis in the MMTV-neu model and whether they respond to curaxin-137 treatment. It was investigated whether FACT expression is different between normal and tumorous mammary epithelial tissue. While in tumor free mammary gland tissue of MMTV-neu animals SSRP1 and SPT16 were very low, in tumors isolated from the same animals higher levels of both subunits were detected (FIG. 2A). Both SSRP1 and SPT16 levels were variable but, in all cases, higher than in tumor free tissue. To identify the stage of tumor formation at which FACT becomes overexpressed in this model, sections of tumor free mammary glands and lesions of different degrees of malignancy were stained with anti-SSRP1 antibodies. As shown in FIG. 2B, SSRP1-positive mammary epithelial cells were detected in sections of tumor-free mammary glands from MMTV-neu mice, but not in similar sections from age-matched wild type animals of the same FVB background. A much higher degree of SSRP1 staining was seen in abnormal mammary lesions of all stages from MMTV-neu mice (FIG. 2B). These data suggest, without wishing to be bound by theory, that FACT levels are elevated early in the process of mammary epithelia transformation in MMTV-neu animals.

p53 plays a role in mammary carcinogenesis. Curaxin-137 causes chromatin trapping of FACT. This leads to both activation of p53 via phosphorylation by FACT-associated Casein Kinase 2 (CK2) and inhibition of NF-κB dependent transcription due to depletion of soluble FACT from the nucleoplasm. The lack of soluble FACT in curaxin-treated cells blocks elongation of NF-κB dependent transcripts, but does not prevent nuclear translocation of NF-κB per se. Moreover blocked NF-κB-dependent transcription leads to the depletion of IκBα normally keeping NF-κB complex in cytoplasm. Therefore, Curaxin treatment leads to accumulation of NF-κB in the nuclei of cells. It should be noted that while nuclear translocation of NF-κB is typically interpreted as a sign of NF-κB activation, in this case, it is actually an indicator of NF-κB inhibition.

Three parameters were used to assess activity of the drug at the molecular level in the MMTV-neu model: (i) reduction of FACT subunit levels in the soluble fraction of nuclear protein extracts; (ii) stabilization (elevation of protein level) of p53; and (iii) nuclear translocation of the p65 subunit of NF-κB.

To evaluate the effect of curaxin-137 on FACT, p53 and NF-κB in tumor-free mammary gland cells and mammary tumor cells of MMTV-neu mice, short term ex vivo cultures were generated from freshly isolated and disaggregated tissue and treated with curaxin-137. As shown in FIG. 2C, ex vivo curaxin-137 treatment resulted in disappearance of both FACT subunits, SSRP1 and SPT16, from soluble nuclear extracts of mammary tumor cells, while little or no SSRP1 or SPT16 protein was detected in tumor free mammary gland extracts (FIG. 2A).

To determine the NF-κB status of mammary tumors from MMTV-neu mice, samples of the same tumors were used for immunofluorescent staining with an antibody against the p65 subunit of NF-κB. Weak background staining was observed in tumor-free mammary gland, while all 5 tumor samples demonstrated visible p65 positivity with cytoplasmic localization in most of the cells and nuclear staining in some cells (FIG. 2D). Curaxin-137 treatment led to significant nuclear relocalization of p65 without any additional stimulus, which is consistent with the previously defined specific mechanism of NF-κB inhibition by curaxin-137 (FIG. 2E).

Evaluation of p53 protein levels in the same ex vivo cultures, showed that p53 levels were increased in a dose-dependent manner 6 hours after curaxin-137 treatment of cells from a tumor-free mammary gland and one out of five mammary tumors (FIG. 2F). The other four tumors assessed showed high basal p53 levels and no induction in response to curaxin-137 treatment, likely due to p53-stabilizing mutations (FIG. 2F). These results suggest that a high proportion of mammary tumors in this model have p53 pathway inactivated presumably by p53 mutations and irresponsive to curaxin-137 treatment.

Therefore it was demonstrated that curaxin-137 has desirable effects on multiple pathways, including FACT, ER, Her2, p53, and NF-κB, which may be involved in mammary carcinogenesis in the MMTV-neu mouse model as well as human breast cancer.

Additionally, it was shown that curaxin-137 can be administered to mice chronically with drinking water. Curaxin-137 is orally available and soluble in water. To establish a regimen of chronic administration for a cancer prevention study, it was tested whether mice could be given the compound in their drinking water. MMTV-neu mice did not refuse drinking solutions of 0.1 or 0.2 mg/ml curaxin-137, consuming the same volume of liquid in a given period of time as mice exposed to negative control water (FIG. 3A). However, less liquid was consumed for more concentrated solutions of curaxin-137. Conversion of the amount of solution consumed by mice into the actual dose of the drug indicated an average daily dose of curaxin-137 of 13.8±2.2 mg/kg for the 0.1 mg/ml solution group as and 28.5±2.5 mg/kg for the 0.2 mg/ml group (FIG. 3B). MMTV-neu mice given solutions of curaxin-137 at these dose levels in place of regular drinking water between 4 and 14 weeks of age showed no difference in weight gain as compared to control animals given negative control water (FIG. 3C). In addition, there were no visual differences between the mice in the curaxin-treated and control groups during this period, except that one mouse had a hunched appearance for 2 days without any other changes in behavior or weight. No morphological differences were found between the study groups upon histopathological examination of internal parenchymal organs at the end of the observation period (10 weeks). Moreover, hierarchical clustering of global gene expression profiles of genes in liver and spleen (these organs were selected as organs with the highest level of curaxin-137 accumulated, see below) showed very little difference between Curaxin-treated and control animals (FIG. 3E). These data indicate that chronic administration of curaxin-137 does not cause any apparent systemic toxicity.

Since concentration of curaxin-137 in drinking water higher than 0.2 mg/kg impeded liquid consumption by mice, this dose (0.2 mg/ml curaxin-137 in drinking water; equivalent to 28.5 mg/kg/day) was defined as the MTD for this administration regimen. This dose was very close to the previously established repetitive MTD for administration to mice by oral gavage (30 mg/kg).

Following administration of 0.1 or 0.2 mg/ml curaxin-137 in drinking water for 10 weeks, the compound was detected in the plasma of mice at a median concentration of 56.2 and 111.2 ng/ml, respectively (equivalent to 0.17 and 0.33 µM, FIG. 9). Substantially higher concentrations of curaxin-137 were found in several mouse organs, with spleen showing the highest levels (1286 and 2414 ng/ml in low and high dose groups respectively (equivalent to 3.8 and 7.2 µM) (FIG. 9).

Curaxin-137 at concentrations exceeding the LC50% for most tumor cells in vitro (0.2-0.6 µM) did not cause any pathological changes in spleen or other organs analyzed (FIG. 4). Therefore, we concluded that chronic administration of curaxin-137 was safe enough to be tested as a tumor preventive regimen.

Further, curaxin-137 delays tumor onset and increases survival in MMTV-neu transgenic mice. Three groups of female MMTV-neu transgenic mice were given (i) regular water throughout their lives ("untreated" control), (ii) 0.1 mg/ml solution of curaxin-137 in water from 4 weeks of age, or (iii) 0.2 mg/ml curaxin-137 in water from 10 weeks of age (FIG. 3D). Several mice in each group (including the untreated control group) died without tumors during the course of the study. The reasons underlying these deaths were not established upon necropsy and histopathological examination. Therefore, these deaths were concluded to be not related to drug administration or tumor formation.

In the control group as well as the 0.1 mg/ml curaxin-137-treated group, mammary tumors started being detected at 23-25 weeks of age (FIG. 5A). In contrast, tumor appearance was delayed until 40 weeks of age in the 0.2 mg/ml curaxin-137-treated group. Despite the fact that the kinetics of initial tumor appearance in the low dose curaxin-treated group was similar to that in the control group, both the low and high dose curaxin-treated groups were statistically different from the control group based on the comparison of Kaplan-Meyers curves of tumor-free survival using Log-rank test (FIG. 5B). The median duration of tumor-free survival was 44 weeks in the control group and 57 and 78 weeks in the low and high dose curaxin-treated groups, respectively (FIG. 5B).

Overall survival of animals treated with curaxin-137 was longer than control animals in both treatment groups (FIG. 5A). Some animals in both curaxin treated groups were still tumor-free at >15 months of age, while no control animals lived longer than 13 months (FIG. 5B; FIG. 10). Besides in house pathological evaluation (FIG. 4), the oldest surviving animals from each group were subjected to blind histopathological evaluation by an independent phenotyping facility (FIG. 10). The oldest curaxin-137-treated animals did not have any abnormalities that were different from those seen in the oldest surviving control mice (FIG. 10). This provides additional support for the general non-toxicity and safety of systemic curaxin administration.

Further, the data showed that curaxin-137 slows the progression of mammary tumors. Histological analyses on mammary glands with tumors isolated from mice in the three study group described in the preceding section when the cumulative tumor size per mouse was close to 2000 mm$^3$ were performed. This approach allowed analysis of tumors which were grown approximately the same time, therefore potential differences in their histology cannot be explained by the differences in tumor appearance. Tumors were excised and the morphology of each tumor was assessed on H&E stained sections. Tumors were graded according to the recommendations of Oncogene 2000 Feb. 21; 19(8):968-88 as "undifferentiated" when the tumor mass was >90% solid cell mass with no traces of cells forming glandular or tubular structures (FIG. 6A), "high grade" when >50% of the tumor mass was comprised of poorly organized, but recognizable glandular-like structures (FIG. 6B) or thick tubular structures (FIG. 6C); "glandular" when 100% of the tumor mass resembled glandular or tubular structures (FIG. 6D) and "carcinoma in situ" when the tumor mass consists primarily of hyperplasic mammary epithelial structures (FIG. 6E and FIG. 6F). Analysis of the proportion of tumors of each type in each study group (control, 0.1 mg/ml or 0.2 mg/ml curaxin-137-treated) demonstrated that more than half of the tumors in the control group had undifferentiated phenotypes and only minor proportions of the tumors were classified as more differentiated subtypes. In contrast, in both curaxin-treated groups, most of tumors were more differentiated subtypes (FIG. 6G). Since loss of differentiation is usually associated with tumor progression, the prevalence of more differentiated tumors in curaxin-137 treated groups of mice shows that chronic administration of the drug slowed tumor progression in the MMTV-neu breast cancer model.

Example 2

Anticarcinogenic Effects of Curaxins

Curaxin 137 (CBLO137) was studied using CBA mice, which were administered 1,2-dimethylhydrazine (DMH) to evaluate their ability to inhibit carcinogenesis. This carcinogen induces tumors of the large intestine, kidneys, uterus, ovaries, perianal skin, liver tumors. The ability of DMH to induce tumors of the large intestine in mice and rats is known in the art. Comparative evaluation of carcinogenic activity of 1,2-DMH was performed using different mouse strains (FIG. 11 and FIG. 12).

The most effective carcinogenic activity of DMH was manifested in CBA mice. DMH induces tumors, in both male and female CBA mice, such as, for example, adenocarcinomas and polyps of large intestine, squamous cell carcinomas of perianal skin, hepatomas and hemangioendotheliomas; tumors. Exemplary DMH-induced tumors typical in female CBA mice include, for example, uterine sarcomas, ovarian adenocarcinomas; exemplary DMH-induced tumors typical in male CBA mice include, for example, angiosarcomas of the adrenal glands and cystic and solid renal adenomas. Thus, this experimental model allows evaluate of curaxin against tumors in different locations. Further this model of chemically-induced tumors translates to human disease indirectly and directly, as 1,2-DMH and its nonsymmetrical analog, 1,1-DMH, are human carcinogens. Hydrazine and its derivatives are officially declared human carcinogens in the Russian Federation laws (Sanitation Regulation and Hygienic norms 1.2.2353-08 "Carcinogenic factors and main requirements to prevention of carcinogenic risk"). 1,1 DMH is widely used in aerospace industry as an important component of rocket fuel. Thousands of people are engaged in its production and usage, many of them are within carcinogen high-risk group because they have symptoms of chronic poisoning by 1,1 DMH. Many carcinogens, indicated as "absolute carcinogens" may not only initiate tumor formation but also to promote its progression. 1,2-DMH is one of such carcinogens.

Without wishing to be bound by theory, curaxins may affect enzymes involved in xenobiotic metabolism, in particular, cytochrome P450 CYP2E1 isoform, which is essential for metabolic activation of 1,2-DMH. Accordingly, curaxins may affect both initiation process and tumor promotion-progression process, induced by 1,2-DMH.

This Example shows the antitumor effects of curaxins upon simultaneous administration with 1,2-DMH or after exposure of animals to 1,2-DMH.

The study involved 152 male mice and 150 female mice. Animals were divided into the following experimental groups: 1) group, to which was administered 1,2-DMH, 2) group, to which was administered 1,2-DMH and Curaxin, 3) group, to which was administered Curaxin, 4) control group (without any administration).

Curaxin administration began 2 weeks after discontinuation of 1,2-DMH administration, when, without wishing to be bound by theory, both carcinogen and its metabolites should be eliminated from the organism. Curaxin was added to drinking water at concentration of 0.20 mg/ml or 0.13 mg/ml, which corresponded to doses 30 and 20 mg/kg. Curaxin solution was prepared daily.

Experimental Groups: CBA male mice (152 mice):1) 30 mice—control (without administration), 2) 37 mice—1,2-DMH, 15 weeks 8 mg/kg, 3) 44 mice—1,2-DMH, 15 weeks, 8 mg/kg, CBL0137, 17-40 weeks, 20 mg/kg, 4) 39 mice—CBL0137, 17-40 weeks, 20 mg/kg; CBA female mice (150 mice): 1) 30 mice—control (without administration), 2) 37 mice—1,2-DMH, 20 weeks 8 mg/kg, 3) 44 mice—1,2-DMH, 20 weeks, 8 mg/kg, CBL0137, 22-42 weeks, 20 mg/kg, and 4) 39 mice—CBL0137, 22-42 weeks, 20 mg/kg.

The experimental design is shown in FIG. 7. Tumors were induced by 1,2-dimethylhydrazine. Curaxin 137 (CBL0137) was administered as indicated.

Evaluation of animal condition throughout the study: beginning from Week 1 of the study (DMH administration) mice were weighted and observed individually several times a week. Mice condition during drug administration was observed by changes in bodyweight and animal motor activity. Dead animals and moribund animals were put to death and necropsied during the study. The amount of administered curaxin solution was evaluated by the remained amount of liquid in the drinking bowl per 1 cage and was calculated as an average for 1 animal.

Necropsy and macroscopic analysis: mice were euthanized according to an approved Animal Study Protocol. During necropsy blood samples were collected, pathologoanatomic macroscopic analysis was performed, a preliminary diagnosis was made, organs were weighed and. Organs were taken (separately for freezing and formalin fixation) from 152 male mice and 150 female mice. Organs of the animals which were found dead during the study (if no decomposition was observed) were fixed in formalin.

Preparation of histological specimens was done as is known in the art. After extraction organs were fixed in 10% buffered formalin (Bio Vitrum) for not less than 3 days. Then tissue samples were dehydrated with alcohol (70°; 96°-1, 96°-2; 100°-1, 100°-2), chloroform (c.p., Vekton) and poured into the Histomix (Histomixextra, BioVitrum). Removing of paraffin and staining of histological samples: Xylol-1, Xylol-2 (m-Xylol, Merck); alcohols (100°, 96°, 70°), hematoxiline-eosin (Haematoxylin, Ferak; Eosin B, Aldrich). Dehydration and balsam embedding of specimens: alcohol (100°, 96°, 70°), xylol-1, xylol-2 (m-Xylol, Merck); mounting medium Bio-Mount-analog of balsam (Bio-Optica).

Animal bodyweight: stable increase of animal bodyweight was observed in all groups from Week 1 to Week 16. Some decrease in average bodyweight was observed during DMH administration from Week 16 to Week 20. After administration of curaxin at a dose of 30 mg/kg all animals were observed to experience a drastic decrease in bodyweight and symptoms of dehydration. On Day 14 in male mice and on Day 7 in female mice due to occurrence of dehydration curaxin administration was discontinued for 10 days in male mice and for 7 days in female mice. Then curaxin administration was performed at a dose of 20 mg/kg till the end of the study; dehydration symptoms were not observed (FIG. 8).

Data of necropsy and macroscopic analysis—Organ weight: weight of organs extracted during the necropsy is shown in FIG. 13 and FIG. 14.

Data on macroscopic analysis of animal organs, male and female, in the study described is shown in FIG. 15 and FIG. 16.

Tumors of large intestines: in control groups of female and male mice and in the animals, which were administered Curaxin, no tumoral transformations were observed. Tumors of the large intestine were found in groups of animals administered DMH: in 22 out of 37 male mice and in 20 out of 39 female mice. The multiplicity of neoplasms in these groups fluctuated from 2 to 5 per animal. In DMH plus curaxin groups tumors were found in 12 out of 44 male mice and in 12 out of 44 female mice.

Renal tumors: renal tumors were observed in 22 male mice in the groups of animals which were administered DMH and in 18 out of 45 male mice in group which was administered DMH plus curaxin. In the group of animals which were administered curaxin and in control group no changes in kidneys were observed. Renal tumors in female mice were only observed in the group of animals administered DMH and only in 1 out of 40 mice.

Liver tumors: male CBA mice are characterized by high incidence rate of spontaneous hepatomas. Administration of DMH induces a significant decrease in the incidence rate of this type of benign tumor, however, by now its mechanism is not completely clear. Curaxin did not have any effect on intensity of spontaneous carcinogenesis in male mice. In control animals (30 male mice) and in the group administered curaxin (40 male mice), the liver tumor incidence rate was $17/30$ (56.7%) and $22/39$ (56.4%), correspondingly. In female CBA mice spontaneous hepatomas develop more rarely than in male mice. In the DMH group incidence rate of hepatomas was $1/39$, and in DMH plus curaxin group it consisted $1/44$. In male mice which were administered DMH and DMH plus curaxin, hemorrhagic neoplasms of liver were rarely developed ($1/37$ and $1/44$ correspondingly). Thus, Curaxin didn't have modulating effect on DMH induction of this kind of tumors. Hemorrhagic neoplasms in liver of female mice developed more often ($6/39$—DMH group and $9/44$—DMH plus curaxin group)

Squamous cell carcinomas of perianal skin: squamous cell carcinomas of perianal skin (anal tumors—AT) are squamous cell cancer which develops from surface epithelium of perianal skin. Some of these tumors may develop, without wishing to be bound by theory, not only from surface epithelium but also from perianal sebaceous (preputial) glands. DMH is an AT inductor. Tumors were observed in 16 out of 37 male mice and in 10 out of 39 mice. Curaxin administration did not induce formation of this kind of tumors and didn't have effect on carcinogenic activity of DMH (tumors were observed in 18 out of 44 male mice and in 15 out of 44 female mice).

Uterine tumors: in the control group and in the group of mice which were administered curaxin, no uterine tumors were observed. In the DMH group, tumor incidence rate and thickening of uterine horn and body was $19/39$ and in DMH plus curaxin group such transformations were observed in 18 out of 44 animals.

Ovarian tumors: maximum incidence rate of transparent cysts was observed in the control group as tumors were found in 9 out of 30 mice. On the contrary, the curaxin group showed 3 out of 40 mice had cysts. Therefore, curaxin had a suppressing effect on incidence rate of transparent ovarian cysts. A similar effect was observed in animals which were administered DMH and DMH plus curaxin (cysts were observed in 6 out of 39 and 6 out of 44 mice correspondingly). Hemorrhagic neoplasms in ovaries were mostly observed (6 out of 39) in the group of mice which were administered DMH. In the group of mice which were administered DMH plus curaxin, the incidence rate of these tumors decreased to 3 out of 44. In the group of mice which were only administered curaxin, no hemorrhagic neoplasms of ovaries were observed and in the control group this kind of tumor was found in 1 out of 30 mice.

Tumors of other organs: in male mice from DMH group one mesenterial tumor was found. In one female mouse which was administered DMH one uterine tumor and stomach tumor of a metastatic origin were observed.

Further, microscopic analysis revealed the following benign and malignant tumors and tumor masses.

Large intestine: glandular polyps and adenocarcinomas were found in male and female mice from DMH and DMH plus curaxin groups.

Histological analysis of the large intestine of mice, to which were administered 1,2-DMH and DMH plus curaxin, revealed development of glandular polyps and adenocarcinomas in both male and female mice. In male mice, significant anticarcinogenic effects of curaxins were manifested in incidence rate of polyps and adenocarcinomas. In the 1,2-DMH group, and 1,2-DMH plus curaxin group percent of mice with polyps was 54.05% and 22.73%, correspondingly. These differences are statistically significant (P<0.01) according to Pearson's chi-squared test ($\chi^2$). During macroscopic analysis many animals were observed to have multiple glandular polyps. In that connection, the number of polyps per animals with polyps was calculated (multiplicity). Multiplicity in large intestine polyp count in DMH group was 1,2 higher than in DMH plus curaxin group (1.80 and 1.50 correspondingly).

In female mice from DMH group glandular polyps were found in 25 out of 35 mice (64.10%) and in DMH plus curaxin group—in 11 out of 44 (25.00%). These differences are also statistically significant (P<0.001). In female mice multiplicity in large intestine polyp count in DMH group exceeded DMH plus curaxin group by 4 times (6.12 and 1.64 correspondingly)/

Glandular polyps develop under influence of 1,2-DMH and are not spontaneous neoplasms. In the model, used in this study, glandular polyps represent glandular epithelial hyperplasia of large intestine, they show exophytic growth, do not penetrate basement membrane and don not damage muscular layer.

Adenocarcinomas of large intestine in male mice were only found in DMH group in 7 out of 37 animals (18.92%). In DMH plus curaxin group these tumors were not observed (0%). These differences are statistically significant (P<0.01).

In female mice large intestine adenocarcinomas were observed in 8 out of 39 mice (20.51%) from DMH group, which is statistically higher in comparison with control group. In DMH plus curaxin group adenocarcinomas were found in 5 out of 44 animals (11.36%). In the DMH group, malignization of some polyps was observed in one animal (multiplicity 1.50) and in DMH plus curaxin group such phenomena was not observed.

Adenocarcinoma of large intestine is a malignant neoplasm of glandular epithelium which is characterized by cellular atypia and invasive growth with penetration of basement membrane and muscular layer.

Kidneys: moreover, in male mice significant anticarcinogenic effect was manifested in decreasing the incidence rate of renal capsule angiosarcomas. Renal adenomas were found in the kidneys of female and male mice from DMH and DMH plus curaxin groups. Male mice were also observed to have of renal capsule angiosarcomas. In male mice from DMH group renal adenomas were found in 94.6% (in 35 out of 37 animals) and in DMH plus curaxin group—in 38 out of 44 animals (86.4%). During microscopic analysis many animals were observed to have several renal adenomas. Multiplicity of renal adenomas in DMH group was 1.5 times higher than in DMH plus curaxin group (3.84 and 2.55 correspondingly).

In female mice from DMH group renal adenomas were observed in 3 out of 39 (7.69%) mice and in DMH plus curaxin group—in 1 out of 44 animals (2.27%).

By histological structure renal adenomas are divided into cystadenomas, papillary cystadenomas and solid adenomas. Mitosis in these tumors is very rare, cellular atypia is not severe, invasive growth into peripheral tissue was absent.

Renal capsule angiosarcomas (RCA) were only found in male mice. In the DMH group RCA were found in 18 out of 37 animals (48.65%) and in the DMH plus curaxin group RCA were found in only in 9 out of 44 (20.45%). These differences are statistically significant (P<0.01).

Histologically at early stages of development of renal capsule angiosarcomas we found subcapsular hemorrhage with artery thrombosis and capillary enlargement in renal capsule. Large tumors represented various histological variants of angiosarcomas. No animal was observed to have metastases.

Liver: formation of spontaneous benign liver tumors—hepatomas—is typical for CBA mice. Hepatomas were found in animals from all experimental and control groups, in both male and female mice. Hepatomas were found in 11 out 37 (29.73%) male mice from DMH group, in 10 out of 44 (22.73%) mice from DMH plus curaxin group, in 22 out of 39 mice (56.41%) from the curaxin group, and in 16 out of 30 (53.33%) mice from the control group. The incidence rate of spontaneous hepatomas in the group which was administered DMH was lower than in curaxin group and control group. However, in the DMH group multiple hepatomas were observed (1.55 multiplicity) which was not observed in other groups. In DMH group—2 out of 39 (5.13%) had hepatomas, in DMH plus curaxin group—2 out of 44 (4.55%), in Curaxin group—1 out of 39 (2.56%), in Control group—1 out of 30 (3.33%).

Histologically hepatoma is a nodule, clearly defined from not transformed liver tissue. Hepatoma is characterized by damages in liver structure, absence of beam structure typical for liver, hepatocytes are with severe atypia, cellular dystrophy and necrosis.

Perianal skin: tumors of perianal skin are one of the most frequent neoplasms induced by DMH in mice. Tumors of perianal skin (anal tumors—AT) are squamous cell cancer, which develops from surface epithelium of perianal skin. Some of such tumors may develop not only from surface epythelium but also from perianal sebaceous (preputial) glands.

In DMH group AT was found in 16 out of 37 male mice (43.24%), in DMH plus curaxin group—in 18 out of 44 animals (40.91%).

In female mice, in the DMH group AT was found in 11 out of 38 animals (28.21%) and in DMH plus curaxin group—in 15 out of 44 animals (34.09%).

Microscopic analysis revealed the histological types of perianal skin tumors described below. The most frequently seen cancer is a squamous cell cancer with cornification and without cornification. Squamous cell cancer with cornification is more differentiated type of cancer than skin cancer without cornification. Preputial gland cancer was only diagnosed in two animals (1 female mouse and 1 male mouse) in DMH group, and in male mouse this tumor metastasized to the lung. An increase of squamous cell cancer with cornification was observed in DMH plus curaxin group in comparison with DMH group. Thus, 7 out of 37 male mice had squamous cell cancer with cornification (18.92%) in DMH group and 16 out of 44 (36.36%) male mice in DMH plus curaxin group. Squamous cell cancer without cornification was found in 8 out of 37 animals (21.62%) in DMH group and only in 2 out of 44 (4.55%) animals in DMH plus curaxin group. In female mice squamous cell cancer with cornification was found in 3 out of 39 mice (7.69%) in DMH group and in 11 out of 44 (25.00%) in DMH plus curaxin group. Squamous cell cancer without cornification was observed in 7 out of 39 mice (17.94%) in DMH group and in 4 out of 44 (9.09%) in DMH plus curaxin group.

Uterus: spontaneous uterine sarcomas in CBA mice develops very rarely and only in mice which are older than 18 months. After DMH administration uterine sarcomas are observed in 50% of mice depending on dose and regimen. The number of uterine sarcomas in DMH group was 1.4 higher than in DMH plus curaxin group. In DMH group uterine sarcomas were found in 13 out of 39 animals (33.33%) and in DMH plus curaxin in 9 out of 44 animals (20.45%). One female mouse from DMH group was observed to have uterine sarcoma with abdominal wall metastasis. Histologically these tumors are defined as stromal sarcomas which develop in endometrial stroma with myometrial invasion. Tumor tissue consisted of elongated fibroblast type cells and areas with immature mesenchymal cells. Abdominal wall metastasis looked like neoplasm protruding into the cavity and microscopically it had structure of fibroblastic sarcoma.

Ovaries: in female CBA mice follicular ovarian cysts develop spontaneously which is associated with accelerated aging of these animals. The maximum incidence rate of transparent cysts was observed in control group (17 out of 39 mice (56.67%)); in the DMH group follicular cysts developed in 11 out of 39 mice (28.31%), in the DMH plus curaxin group follicular cysts developed in 9 out of 44 (20.45%) mice; in the curaxin group follicular cysts developed in 15 out of 39 mice (38.46%). Thus, DMH reliably decreases number of follicular cysts while curaxin intensifies its action.

Besides follicular cysts, female mice from experimental and control groups experienced damages of ovaries, caused by hemorrhagic cysts and hemangiomas. Hemorrhagic cysts developed in all groups except the curaxin group. In the DMH group hemorrhagic cysts were found in 3 out of 39 mice (7.69%), in the DMH plus curaxin hemorrhagic cysts were found in 5 out of 44 (11.36%) and in the control group hemorrhagic cysts were found in 4 out of 30 (13.33%). Hemangiomas were only observed in the DMH group (in 5 female mice out of 39-12.82%) and in the DMH plus curaxin group (in 1 female mouse out of 44-2.27%). Though the number of hemangiomas in DMH group exceeded their number in the DMH plus curaxin group by 5 times.

Lungs: in the lungs benign neoplasms were observed, these adenomas, which are spontaneous in linear mice, develop quite rarely in CBA mice. In male mice, DMH induced spontaneous adenomagenesis in the lungs, and curaxin did not have any effect on it. In DMH group adenomas were observed in 7 out of 27 animals (18.92%, P<0.05 in comparison with control), in DMH plus curaxin—in 7 out of 44 (15.91%, P>0.05, in comparison with control), in control group—in 1 out of 30 (3.33%) mice. In Curaxin group lung adenomas were not found. In female mice from the DMH group adenomas were observed in 3 out of 39 animals (7.69%), in the DMH plus curaxin group adenomas were observed in 2 out of 44 (4.55%), in the Curaxin group adenomas were observed in 1 out of 39 animals (7.69%). In the control group, adenomas were not found.

Spleen: microscopic analysis of spleen was performed in all female and male mice. No pathological changes were observed in this organ.

Accordingly, this Example shows, inter alia, that curaxins had anticarcinogenic effect after induction of large intestine tumors by 1,2-dimethylhydrazine: the incidence rate of adenomatous polyps decreased in male mice from 54.05% to 22.73%, in female mice from 64.4% to 25% and then incidence rate of adenocarcinomas in male mice decreased from 18.9% to 0%, in female mice from 20.51% to 11.3%. Further this Example shows, inter alia, that curaxins induced a decrease of multiplicity in formation of adenomatous polyps in male mice—by 1.2 times, in female mice—by 4 times. Additionally this Example shows, inter alia, that curaxins decreased incidence rate of renal capsule angiosarcomas in male mice from 48.65% to 20.45%. Further still, this Example shows, inter alia, that curaxin administration decreased the incidence rate of uterine sarcomas, induced by DMH from 33.33% to 20.45%. Additionally, this Example shows, inter alia, that curaxins do not have a pro-carcinogenic effect.

EQUIVALENTS

Those skilled in the art will recognize, or be able to ascertain, using no more than routine experimentation, numerous equivalents to the specific embodiments described specifically herein. Such equivalents are intended to be encompassed in the scope of the following claims.

INCORPORATION BY REFERENCE

All patents and publications referenced herein are hereby incorporated by reference in their entireties.

What is claimed is:

1. A method for treating a carcinogen-induced cancer in a subject in need thereof, comprising administering to the subject an effective amount of a compound of the formula:

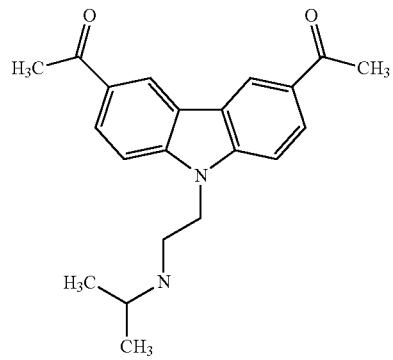 [SMILES: CC(=O)c1ccc2c(c1)c1cc(C(C)=O)ccc1n2CCNC(C)C]

or a pharmaceutically acceptable salt or hydrate thereof, wherein:
the carcinogen is a genotoxic carcinogen and
the cancer is selected from colon, renal and uterine cancer.

2. The method of claim 1, wherein the cancer is colon cancer.

3. The method of claim 1, wherein the cancer is renal cancer.

4. The method of claim 1, wherein the cancer is uterine cancer.

5. The method of claim 1, wherein the genotoxic carcinogen is a hydrazine.

6. The method of claim 5, wherein the hydrazine is dimethylhydrazine.

7. The method of claim 6, wherein the dimethylhydrazine is 1,2-dimethylhydrazine.

* * * * *